(12) United States Patent
Hangody et al.

(10) Patent No.: US 6,375,658 B1
(45) Date of Patent: Apr. 23, 2002

(54) CARTILAGE GRAFTING

(75) Inventors: Lazlo Hangody; Zoltan Karparti, both of Budapest (HU); Paul Alexander Torrie, Marblehead; Michael Ferragamo, N. Dighton, both of MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 09/559,532

(22) Filed: Apr. 28, 2000

(51) Int. Cl.[7] .............................................. A61B 17/56
(52) U.S. Cl. ............................ 606/80; 606/96; 606/99; 623/20.18
(58) Field of Search .............................. 606/60, 72, 80, 606/96, 99, 104; 623/20.14, 20.18, 908

(56) References Cited

U.S. PATENT DOCUMENTS

| | | |
|---|---|---|
| 4,349,058 A | 9/1982 | Comparetto |
| 4,708,139 A | 11/1987 | Dunbar, IV |
| 4,710,075 A | 12/1987 | Davison |
| 5,163,940 A | 11/1992 | Bourque |
| 5,190,548 A | 3/1993 | Davis |
| 5,207,681 A | 5/1993 | Ghadjar et al. |
| 5,269,785 A | 12/1993 | Bonutti |
| 5,405,348 A | 4/1995 | Anspach, Jr. et al. |
| 5,484,437 A | 1/1996 | Michelson |
| 5,489,307 A | 2/1996 | Kuslich et al. |
| 5,490,852 A | 2/1996 | Azer et al. |
| 5,569,262 A | 10/1996 | Carney |
| 5,573,537 A | 11/1996 | Rogozinski |
| 5,575,794 A | 11/1996 | Walus et al. |
| 5,603,716 A | 2/1997 | Morgan et al. |
| 5,632,745 A | 5/1997 | Schwartz |
| 5,785,714 A | 7/1998 | Morgan et al. |
| 5,919,196 A | 7/1999 | Bobic et al. |
| 5,951,559 A | 9/1999 | Burkhart |
| 6,019,767 A | 2/2000 | Howell |

FOREIGN PATENT DOCUMENTS

| | | |
|---|---|---|
| DE | 202970 | 10/1983 |
| DE | 8708304 | 9/1987 |
| DE | 19503504 | 3/1996 |
| EP | 0307241 | 3/1989 |
| EP | 0508710 | 10/1992 |
| EP | 0824893 | 2/1998 |
| FR | 2699068 | 6/1994 |
| FR | 2732210 | 10/1996 |
| HU | 80004-5072 ER | 9/1994 |
| RU | SU298673 | 12/1982 |
| WO | 96/24302 | 8/1996 |
| WO | 96/27333 | 9/1996 |
| WO | WO98 34569 | 8/1998 |
| WO | WO99 29237 | 6/1999 |

OTHER PUBLICATIONS

Vladimir Bobic, MD.; "The Utilization of Osteochondral Autografts in the Treatment of Articular Cartilage Lesions"; The Arthrex Solution to Osteochondral Autograft Transfer System (OATS™);AAOS 65th Annual Meeting, New Orleans, Mar. 19–23, 1998; Instructional Course No.: 146 (12 pp).

(List continued on next page.)

Primary Examiner—David O. Reip
(74) Attorney, Agent, or Firm—Fish & Richardson P.C.

(57) ABSTRACT

A set of surgical instruments for repairing a cartilage surface on a posterior surface of the patella includes a first instrument and a second instrument. The first instrument includes a channel defining a longitudinal axis that extends from the channel to intersect an anterior surface of the patella. The second instrument is mountable to the first instrument and includes a surface that is configured to be placed against a posterior surface of the patella. The longitudinal axis of the channel is at an angle to the surface of the second instrument when the second instrument is mounted in the first instrument.

17 Claims, 21 Drawing Sheets

OTHER PUBLICATIONS

Arthrex, "Finally, An Arthroscopic Treatment For Osteochondral Lesions," Arthroscopic Osteachondral Autograft Transplantation in ACL Reconstruction: A preliminary Study, 1996.

Beadling et al., World of Opportunity for Osteochondral Transplantation, Sports Medicine, Sep. 1996.

Innovasive, "Innovasive COR System", ; Ordering Information, Sep. 1996.

Innovasive, "Innovasive COR System", Innovasive COR Repair System, Catalog No. 3510, Oct. 1996.

"Innovasive COR System: An Arthroscopic Technique for Harvesting & Transplanting Bone Grafts", Innovasive Instructional Technique, Sep. 1996.

Innovasive, Instructional Insert Innovasive COR System, Doc. #50000275 rev. A.

Instrument Maker, "Biologically Quiet, Superior Biodegradable Implants for ACL Reconstruction", 1996 Catalog, p. 22.

Kalb et al.., "Hope for Damaged Joints", Newsweek, Medicine, Jan. 29, 1996, p. 55.

Matsusue et al., "Arthroscopic Multipkle Osteochondral Transplantation to the Chondral Defect in the Knee Associated with Anterior Cruciate Ligament Disruption", Jour. Arth. & Related Surg. 93(3) pp. 318–321.

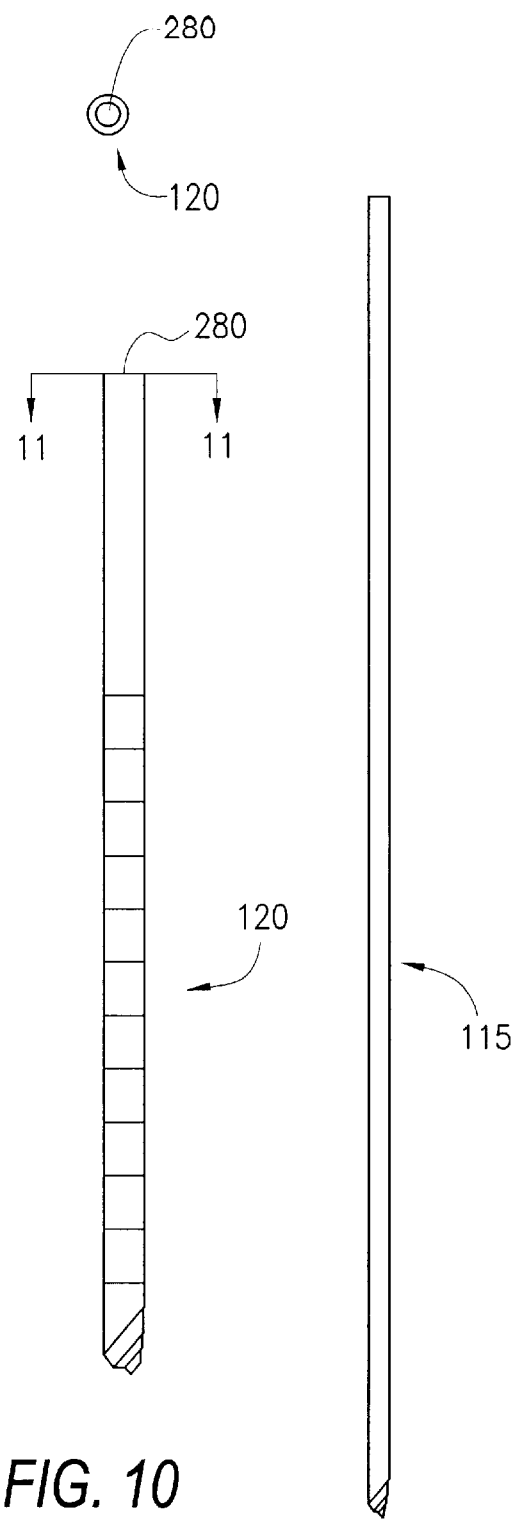
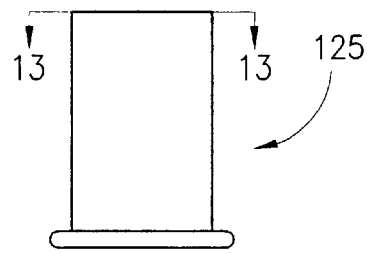
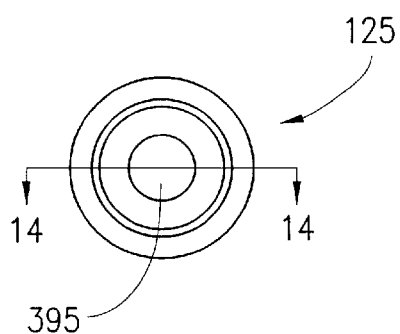
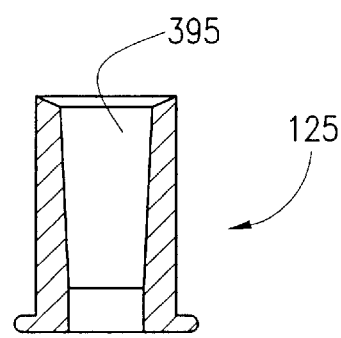
FIG. 11
FIG. 12
FIG. 13
FIG. 14
FIG. 10
FIG. 9

CARTILAGE GRAFTING

TECHNICAL FIELD

This invention relates to repairing cartilage, for example, articular cartilage on the patella and tibia.

BACKGROUND

Articular cartilage that is damaged (e.g., torn or excessively worn) may be repaired in a variety of ways. For example, the damaged cartilage may be shaved or scraped from the bone surface, thereby causing bleeding which stimulates the growth of fibrocartilage. Similarly, small holes may be drilled in the bone to promote bleeding and fibrocartilage growth. Alternatively, an allograft (e.g., cartilage grown in vitro from cartilage tissue removed from the patient) may be implanted by attaching a periosteum membrane (harvested, e.g., from the patient's tibia) to the bone surface and injecting the allograft beneath the membrane. The periosteum provides a healthy environment which promotes further cartilage cell growth.

SUMMARY

In one general aspect, a set of surgical instruments for repairing a cartilage surface on a posterior surface of the patella includes a first instrument and a second instrument. The first instrument includes a channel defining a longitudinal axis that extends from the channel to intersect an anterior surface of the patella. The second instrument is mountable to the first instrument and includes a surface that is configured to be placed against a posterior surface of the patella. The longitudinal axis of the channel is at an angle to the surface of the second instrument when the second instrument is mounted in the first instrument.

Embodiments of the set of surgical instruments may include one or more of the following features. For example, the angle may be between approximately 80° and 100°. The angle also may be at approximately 90°. The set of surgical instruments may further include a guide wire configured to be inserted into the channel in the first instrument and to drill a passage from an anterior opening on the anterior surface of the patella to a posterior opening on the posterior surface of the patella. The longitudinal axis of the passage through the patella is at an angle to the posterior surface of the patella at the posterior opening. The angle may be between approximately 80° and 100°. The angle also may be at approximately 90°. The set of surgical instruments may still further include a drill that can be passed over the guide wire and into the anterior opening. The drill is operable to enlarge the passage in the patella, from the anterior opening to the posterior opening.

The set of surgical instruments may still further include a delivery instrument to deliver a cartilage graft into the passage in the patella. The delivery instrument has an interior channel passage that extends between an open distal end and an open proximal end, and a flange at the distal end. The flange can be inserted into the anterior opening to deliver the cartilage graft through the interior channel into the passage in the patella. The delivery instrument may include a window formed in a wall. The window is open to the interior channel such that the cartilage graft can be observed through the window during delivery through the interior channel.

The set of surgical instruments may still further include an insertion instrument that is insertable into the interior channel of the delivery instrument to advance the cartilage graft from the delivery instrument through the anterior opening in the patella into the passage in the patella.

The first instrument may be a director handle that includes the channel and a slot that receives the second instrument. The second instrument may be a guide that includes a foot that is flush with a posterior surface of the patella when the foot is pressed against the patella. The foot may include a lower surface and a generally flat upper surface opposite the lower surface, with the foot configured to be pressed against the posterior surface of the patella. The generally flat upper surface may include a central channel passing between an opening in the upper surface and an opening in the lower surface. The central channel may have a diameter that is reduced from the upper surface to the lower surface. A longitudinal axis of the central channel may be perpendicular to the generally flat upper surface of the foot. The distal foot may be pivotably attached to the guide.

The set of surgical instruments may further include a tube having an interior channel. The tube may be configured to be inserted into the channel of the director handle and to receive a guide wire in the interior channel for drilling a hole in the patella.

The set of surgical instruments may further include a drill having an interior channel. The interior channel is designed to be inserted over a guide wire to enlarge a hole drilled by the guide wire in the patella.

The set of surgical instruments may further include an offset tool that includes a handle, a probe, and a guide. The handle has a distal end and the probe is attached to the distal end and extends perpendicularly from a face of the handle. The guide is attached to the distal end of the handle, offset from the probe, and has an inner shaft with a longitudinal axis that is substantially parallel to the probe. The longitudinal axis of the guide is offset from a longitudinal axis of the probe by approximately 0.1 to 0.3 inches. The longitudinal axis of the guide may be more particularly offset from the longitudinal axis of the probe by approximately 0.18 inches.

The set of surgical instruments may further include a chisel, a chisel guard, and a tamp. The chisel has a tip and a longitudinal shaft passing through the tip. The chisel guard has a shaft and a flanged end. The chisel guard can be placed around the chisel by inserting the chisel into the chisel guard's shaft. The tamp is designed to be inserted into the longitudinal shaft of the chisel.

The set of surgical instruments may further include a tapered bone plug compressor. The compressor includes a longitudinal shaft passing between a first opening and a second opening, and the diameter of the shaft increases from the second opening to the first opening.

In another embodiment of the set of surgical instruments, the first instrument may be a guide tube and the second instrument may be a clamp body. The guide tube includes the channel and a window that allows visual inspection of the channel. The clamp body includes an upper arm and a lower arm connected by an extension. The upper arm includes a channel having a longitudinal axis and in which the guide tube is inserted. The lower arm includes a foot having a channel aligned with the longitudinal axis of the channel of the guide tube and of the channel of the upper arm.

The upper arm and the lower arm may be connected to the extension at right angles. The upper arm may be connected to the extension such that the upper arm and the lower arm are parallel. The guide tube may be threadably received in the channel in the upper arm.

The foot may have a flat upper surface that is configured to contact a bony surface. The foot may have a flat upper surface that is perpendicular to the longitudinal channel of the guide tube. The foot may be mounted to the lower arm in a fixed relationship or a pivotal relationship. The foot also may be in the form of a ring having a channel through it.

The set of surgical instruments may further include a drill guide, having a longitudinal channel, which is designed to be inserted into the channel in the guide tube. The set of surgical instruments may still further include a guide wire that is insertable into the longitudinal channel of the drill guide.

In another general aspect, a surgical method of repairing an articular cartilage surface on a posterior surface of the patella includes placing a first instrument through a first incision so that the first instrument is adjacent to an anterior surface of the patella, placing a second instrument through a second incision so that the second instrument is located between the posterior surface of the patella and the femoral head, drilling a passage from the anterior surface of the patella to the posterior surface of the patella, inserting a graft into the anterior surface opening of the passage, and inserting the graft further into the passage. The passage passes between an anterior surface opening and a posterior surface opening.

Embodiments of the surgical method may include one or more of the following features. For example, the passage through the patella may be perpendicular to the posterior surface of the patella adjacent to the posterior surface opening. The first instrument may include a channel having a longitudinal axis that extends from the channel to the anterior surface opening of the patella, and through which a guide wire can be inserted to drill the passage through the patella. The second instrument may be mountable to the first instrument and may include a surface that is configured to be placed against a posterior surface of the patella. When the second instrument is mounted in the first instrument, the longitudinal axis of the channel of the first instrument is perpendicular to the surface of the second instrument.

The surgical method may further include enlarging the drilled passage through the patella. Enlarging the passage includes passing a drill over the guide wire, inserting the drill into the anterior surface opening, and enlarging the passage between the anterior surface opening and the posterior surface opening.

In the surgical method, inserting the graft into the anterior surface opening of the passage may further include placing a delivery instrument against the anterior surface opening. The delivery instrument includes an interior channel that extends between an open distal end and an open proximal end, and a flange at the distal end. The flange is designed to be inserted into the anterior surface opening to deliver a cartilage graft through the interior channel into the passage in the patella. The delivery instrument may include a window that is formed in a wall and is open to the interior channel such that the cartilage graft can be visually inspected during delivery through the interior channel. Inserting the graft further into the passage may include inserting an insertion instrument into the interior channel of the delivery instrument and advancing the cartilage graft from the delivery instrument into the passage in the patella through the anterior opening in the patella.

In the surgical method, the first instrument may be a director handle and a tube, and the second instrument may be a patellar guide that includes a foot having a generally flat surface. The first and second instruments are assembled by installing the patellar guide in a slot of the director handle and inserting the tube in a channel of the director handle. Placing the first instrument adjacent to the anterior surface of the patella includes placing a distal end of the tube against the anterior surface of the patella through a first incision. Placing the second instrument adjacent to the posterior surface of the patella includes inserting the second instrument in a second incision and placing the generally flat surface of the foot against the posterior surface of the patella.

The surgical method may further include inserting a guide wire through a longitudinal channel of the tube, inserting the guide wire into the first incision, and drilling a passage with the guide wire through the patella. The passage passes between the anterior surface and the posterior surface of the patella. The passage through the patella may be perpendicular to the posterior surface of the patella. The guide wire may enter a channel in the foot when the guide wire passes through the posterior surface of the patella.

The surgical method may further include removing the director handle and the patellar guide and inserting a drill over the guide wire to enlarge the passage through the patella. The surgical method also may further include drilling at least one additional passage through the patella, with the additional passage being offset from the first passage.

Drilling the additional passage may include providing an offset tool, placing the probe in the first passage, placing the guide wire through the bullet and the inner shaft of the guide, and drilling the additional passage. The offset tool includes a handle having a distal end, a probe attached to the distal end and extending perpendicularly from a face of the handle, and a guide attached to the distal end. The guide is offset from the probe and has an inner shaft with a longitudinal axis that is substantially parallel to the probe. The additional passage is drilled such that it is offset from the first passage by an offset distance from the probe and the longitudinal axis of the inner shaft.

The surgical method may further include harvesting a cartilage replacement graft. Harvesting the cartilage graft may include providing a chisel, a chisel guard, and a tamp. The chisel has a tip and a hollow longitudinal shaft passing through the chisel. The chisel guard has a hollow shaft and a flanged end. The chisel guard's shaft is configured to surround the chisel. The tamp is configured to be inserted into the longitudinal shaft of the chisel and the chisel is used to remove a cartilage graft from a surface of a bone. The cartilage graft includes a cartilage surface and a bony shaft.

The surgical method may further include transplanting the cartilage graft into the passage in the patella from the anterior surface of the patella to the posterior surface of the patella.

In another general aspect, a set of surgical instruments for repairing a tibial articulating cartilage surface includes a first instrument and a second instrument. The first instrument includes a channel having a longitudinal axis. The second instrument is mountable to the first instrument and includes a surface that is configured to be placed flush against the tibial plateau. The longitudinal axis of the channel intersects a surface of the tibial shaft and the tibial articulating surface, and forms a predetermined oblique angle with the tibial articulating surface when the surface of the second instrument is flush against the tibial plateau.

Embodiments of the set of surgical instruments may include one or more of the following features. For example, the set of surgical instruments may further include a guide wire configured to be inserted into the channel and to drill an opening in the surface of the tibial shaft along the longitudinal axis. The guide wire may be configured to drill a tibial passage from the opening in the surface of the tibial shaft to an opening in the tibial articulating surface. The drilled tibial passage has the predetermined oblique angle with the tibial articulating surface.

The second instrument may include an arm that includes the surface, with the surface being configured to be placed against the tibial plateau by passing the surface and a portion of the arm below a meniscus and above the tibia. In another implementation, the second instrument may include an arm that includes the surface, with the surface being configured to be placed against the tibial plateau by passing the surface and a portion of the arm above a meniscus and below the femur. The surface also may be in the form of a ring having a channel or it may have a solid surface.

The set of surgical instruments may further include a delivery instrument that is configured to deliver a cartilage graft into the drilled tibial passage. The delivery instrument includes an interior channel, which extends between an open distal end and an open proximal end, and a flange at the distal end. The flange is configured to be inserted into the anterior opening to deliver a cartilage graft through the interior channel into the tibial passage. The delivery instrument may include a window formed in a wall and open to the interior channel. By viewing the window, the cartilage graft can be visually inspected during delivery through the interior channel.

The set of surgical instruments may further include an insertion instrument that is configured to be inserted into the interior channel of the delivery instrument to advance the cartilage graft from the delivery instrument into the anterior opening in the tibia.

In another implementation of the set of surgical instruments, the first instrument may be a director handle and the second instrument may be a guide. The director handle includes the channel and a slot into which the second instrument is installed. The guide includes an arm and a distal foot, with the arm configured to be adjacent to a femoral condyle and the foot configured to be flush with a tibial plateau when the foot is pressed against the tibial plateau. The foot includes a surface including a pin projecting from the surface and configured to be pressed into the tibial plateau when the foot is pressed against the tibial plateau.

The set of surgical instruments may further include a tube configured to be inserted in the channel and to receive a guide wire for drilling a passage through the tibia to the tibial articulating surface. The passage forms an oblique angle with the tibial articulating surface. The oblique angle may be approximately 30°.

The set of surgical instruments may further include a drill having a central shaft, with the shaft being configured to be inserted over a guide wire to enlarge a hole drilled by the guide wire. The set of surgical instruments may still further include an offset tool that includes a handle having a distal end, a probe, and a guide. The probe is attached to the distal end and extends perpendicularly from a face of the handle. The guide is attached to the distal end, offset from the probe, and has an inner shaft with a longitudinal axis that is substantially parallel to the probe. The longitudinal axis of the guide is offset from a longitudinal axis of the probe by approximately 0.1 to 0.3 inches. More particularly, the longitudinal axis of the guide may be offset from the longitudinal axis of the probe by approximately 0.18 inches.

The set of surgical instruments may further include a chisel, a chisel guard, and a tamp. The chisel has an angled tip and a longitudinal shaft passing through the chisel and the tip. A longitudinal axis of the longitudinal shaft forms an oblique angle with a cross-sectional surface of the tip. The chisel guard has a shaft and a flanged end, and the shaft is configured to surround the chisel. The tamp is configured to be inserted into the longitudinal shaft of the chisel. The oblique angle may be approximately 30°.

The set of surgical instruments may further include a tapered bone plug compressor. The compressor includes a longitudinal shaft passing between a first opening and a second opening, and the diameter of the shaft increases from the second opening to the first opening.

In another general aspect, a surgical method of repairing a tibial articular cartilage surface includes placing a first instrument through a first incision so that the first instrument engages a surface of the tibial shaft, placing a second instrument through a second incision so that the second instrument is located on the tibial plateau, drilling a passage from the surface of the tibial shaft to the tibial articular cartilage surface, inserting a graft into the tibial shaft surface opening of the passage, and inserting the graft further into the passage. The passage passes between a tibial shaft surface opening and a tibial articular cartilage surface opening.

In the surgical method, the first instrument may include a channel having a longitudinal axis that is configured to intersect the surface of the tibial shaft and the tibial articulating surface. The second instrument is mounted to the first instrument and includes a surface that is configured to be placed flush against the tibial plateau. The longitudinal axis of the channel forms a predetermined oblique angle with the tibial articulating surface when the surface of the second instrument is flush against the tibial plateau. Drilling the passage from the surface of the tibial shaft to the tibial articular cartilage surface further includes inserting a guide wire into the channel in the first instrument and drilling an opening in the surface of the tibial shaft along the longitudinal axis. The surgical method may further include drilling the passage from the opening in the surface of the tibial shaft to an opening in the tibial articulating surface. The drilled passage may be at the predetermined oblique angle with the tibial articulating surface. The predetermined oblique angle may be approximately 30°.

The second instrument may include an arm that includes the surface. The surface is placed against the tibial plateau by passing the surface and a portion of the arm below a meniscus and above the tibia. In another implementation, the second instrument includes an arm that includes the surface, and the surface is placed against the tibial plateau by passing the surface and a portion of the arm above a meniscus and below the femur.

In the surgical method, inserting the graft into the tibial shaft surface opening of the passage may further include placing a delivery instrument into the tibial shaft surface opening. The delivery instrument includes an interior channel that extends between an open distal end and an open proximal end, and a flange at the distal end. The flange is configured to be inserted into the opening to deliver a cartilage graft through the interior channel. The delivery instrument may further include a window formed in a wall and open to the interior channel such that the cartilage graft can be visually inspected during delivery through the interior channel. Inserting the graft further into the channel includes inserting an insertion instrument into the interior channel of the delivery instrument to advance the cartilage graft from the delivery instrument into the tibial shaft surface opening in the tibia.

The set of surgical instruments provides numerous advantages. For example, using the patellar guide in a surgical procedure enables the surgeon to repair the posterior surface of the patella in a retrograde manner, which reduces the invasive nature of such a repair. Specifically, because the channel in which a replacement graft is to be inserted can be accessed from the anterior surface of the patella, the patella does not need to be turned over and accessed from the posterior side. In this manner, the procedure is less invasive. Because the channel can be drilled such that it is perpendicular to the opening of the channel on the posterior patellar surface, a cartilage graft should be harvested such that its cartilage surface is perpendicular to its bony length. Thus, when the cartilage graft is inserted into the channel, it will have the cartilage surface flush with the posterior patellar surface, which promotes healing and provides better results.

In using the set of surgical instruments for repairing damaged cartilage on the tibia in the knee, a channel is drilled from the anterior surface of the tibia to the tibial articulating surface of the knee joint. The guide and handle are configured to form a channel having a known angle with the tibial articulating surface. Thus, if a graft is harvested at the same angle and implanted in the channel, its cartilage surface will be flush with the tibial articulating surface in which it is placed.

The details of various embodiments of the invention are set forth in the accompanying drawings and the description below. Other features and advantages of the invention will be apparent from the description and drawings, and from the claims.

DESCRIPTION OF DRAWINGS

FIG. 9 is a front view of a guide wire.

FIG. 10 is a front view of a drill.

FIG. 11 is a top view of the drill of FIG. 10 taken along section line 11—11.

FIG. 12 is a front view of a tapered bone plug compressor.

FIG. 13 is a top view of the tapered bone plug compressor of FIG. 12 taken along section line 13—13.

FIG. 14 is a cross-sectional front view of the tapered bone plug compressor of FIG. 13 taken along section line 14—14.

Like reference symbols in the various drawings indicate like elements.

DETAILED DESCRIPTION

Figure 1:
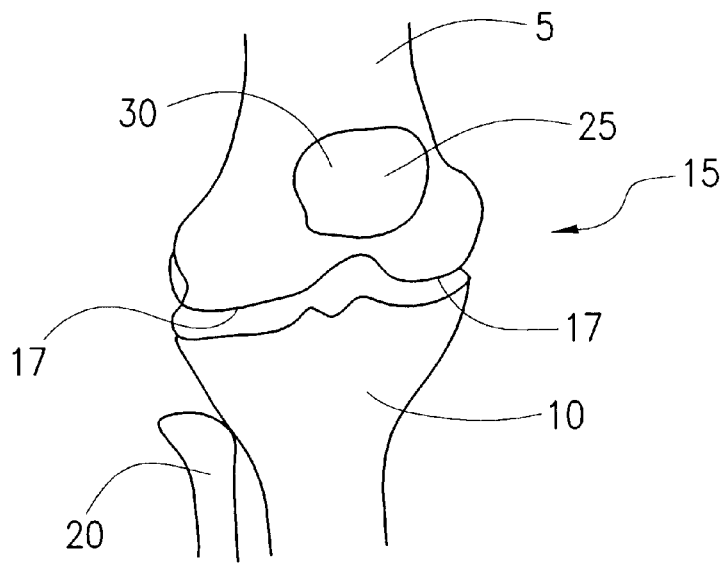
FIG. 1 is a front view of a knee joint showing a femur, a tibia and a patella.
Figure 2:
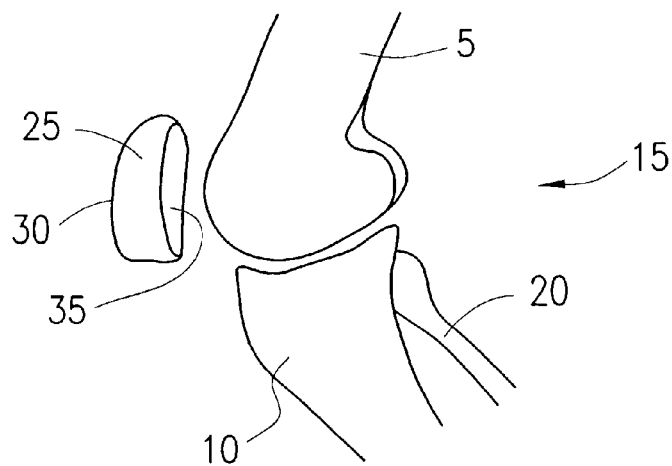
FIG. 2 is a side view of the knee joint of FIG. 1.
Figure 3:
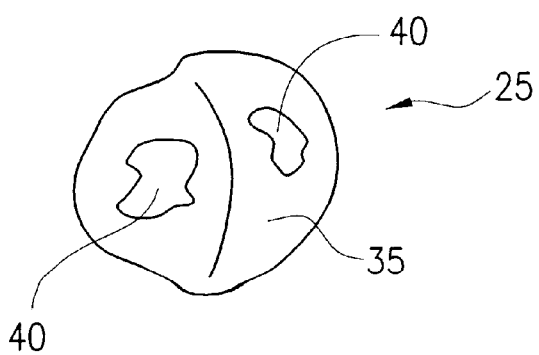
FIG. 3 is a posterior view of the patella of FIG. 1.

Referring to FIGS. 1–3, the femur 5 is connected to the tibia 10 at the knee joint 15, and articulates against the tibia on a pair of femoral condyles 17. The fibula 20 is adjacent to the tibia 10. The patella 20 is located in front of the knee joint 15 adjacent to the femur 5 and is held in position by tendons. The patella 20 provides an articulating surface for the femur 5 to articulate against when flexing the knee joint 15. The patella includes an anterior surface 30 and a posterior surface 35, which contains articular cartilage 40. There is articular cartilage essentially everywhere that two bony surfaces move against one another, i.e., articulate.

In general, articular cartilage covers the ends of the bones in the articulating joint, and is a white, shiny material with a rubbery consistency. The function of articular cartilage is to absorb shock and provide an extremely smooth bearing surface to facilitate motion. In the knee joint 15, articular cartilage covers the ends of the femur, the top of the tibia and the posterior surface 35 of the patella 25, and protects the articulating surfaces from wear and mechanical shock. Because it is subject to wear and mechanical shock, areas of articular cartilage may become damaged (e.g., torn or excessively worn). Damaged areas may be repaired by removing the damaged articular cartilage and implanting healthy cartilage harvested from a donor site, such as from another articulating surface of the femur or tibia.

To ensure that the grafted healthy cartilage follows the contour of surrounding cartilage, the bone and cartilage grafts must be formed as close as reasonably possible to perpendicular to the articular surface, and the graft-receiving holes must also be drilled to a similar degree of perpendicularity to the articular surface. In addition, grafts must be inserted to the proper depth so that the grafted cartilage neither protrudes nor is recessed from the surrounding cartilage. Other deviations from perpendicular also will function and a deviation of approximately 5° to 10° away from 90° likely will function. Deviations more or less than that range may function adequately depending on the characteristics of the graft, including hardness of the graft and thickness of the cartilage, and the surrounding tissue into which the graft is implanted. The instruments and surgical methods described below achieve these goals.

An arthroscopic method for replacing damaged or defective cartilage, such as on one or more areas 40 of damaged articular cartilage on the posterior surface 35 of the patella 25, includes using specialized tools to drill a hole for a recipient graft and to place the recipient graft. The method and tools ensure that the surface of the recipient graft is flush with the posterior surface 35 of the patella 25.

Figure 4:
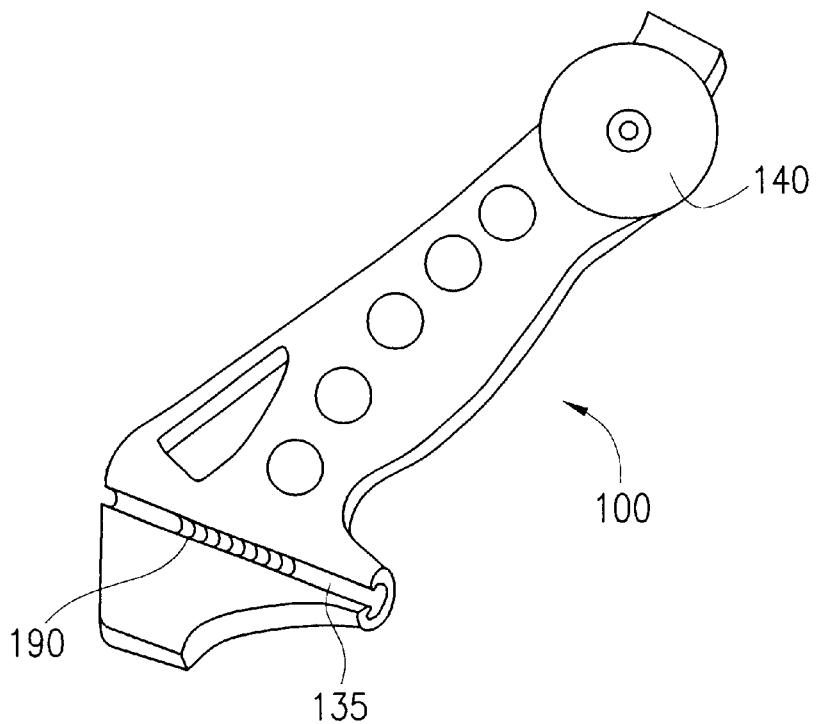
FIG. 4 is a front perspective view of a director handle.
Figure 5:
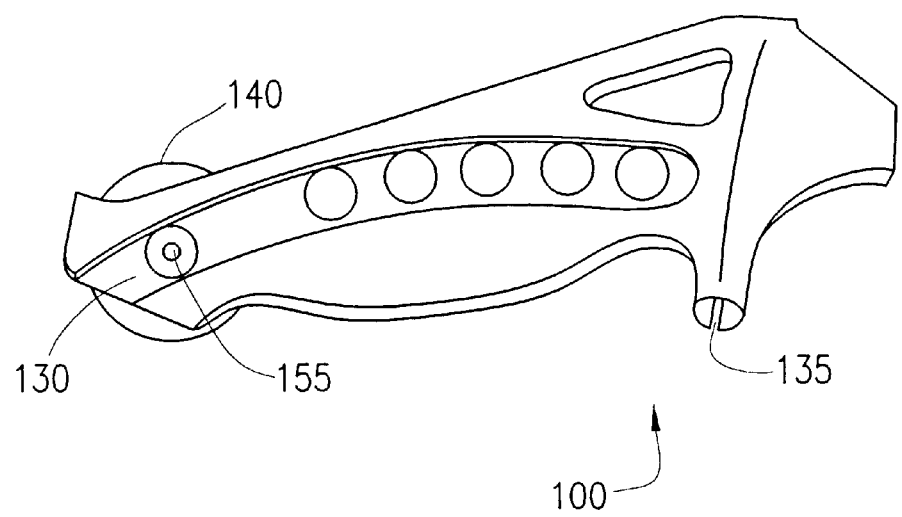
FIG. 5 is a rear perspective view of the director handle of FIG. 4.
Figure 6:
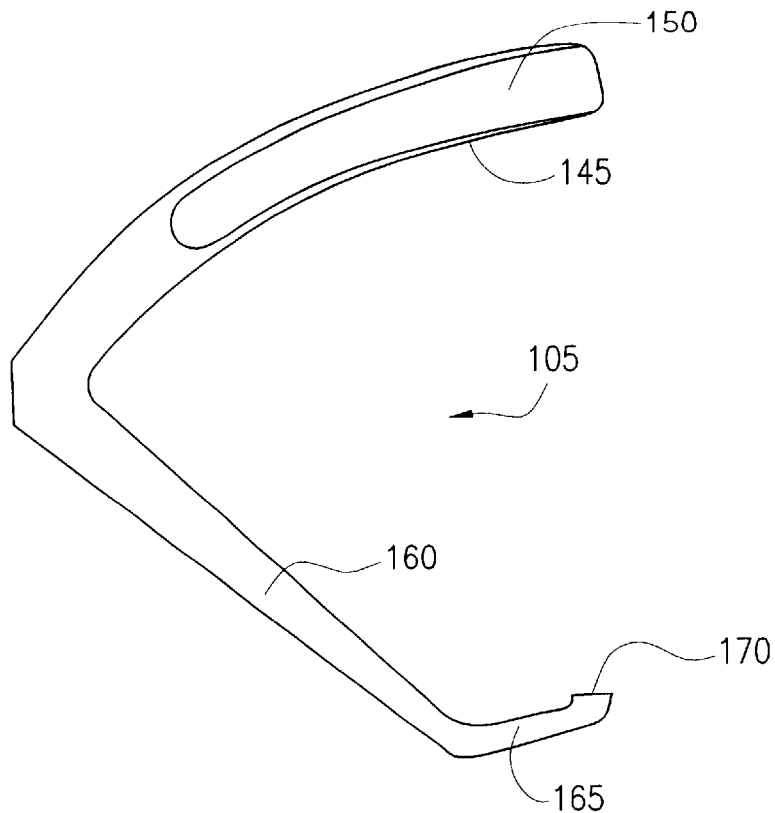
FIG. 6 is a front view of a patellar guide.

FIGS. 4–17 show various views of a specialized set of surgical instruments for repairing the areas of damaged articular cartilage 40. The surgical instruments include a director handle 100 (FIGS. 4 and 5), a patellar guide 105 (FIG. 6), a bullet 110 (FIGS. 7 and 8), a guide wire 115 (FIG. 9), a drill 120 (FIGS. 10 and 11), and a bone plug compressor 125 (FIGS. 12–14). The director handle 100 includes a deep slot 130, a channel 135, and a thumb wheel screw 140. The patellar guide 105 includes an arm 145 having a shallow slot 150.

To install the patellar guide 105 into the director handle 100, the guide's arm 145 is inserted into the deep slot 130 with the shallow slot 150 facing the deep slot 130. By turning the thumb wheel screw 140 clockwise, an end 155 of the thumb wheel screw is forced against the arm 145 in the shallow slot, which fixes the position of the guide 105 relative to the director handle 100. The position of the guide 105 relative to the director handle 100 can be set over a wide range of positions.

Figure 15:
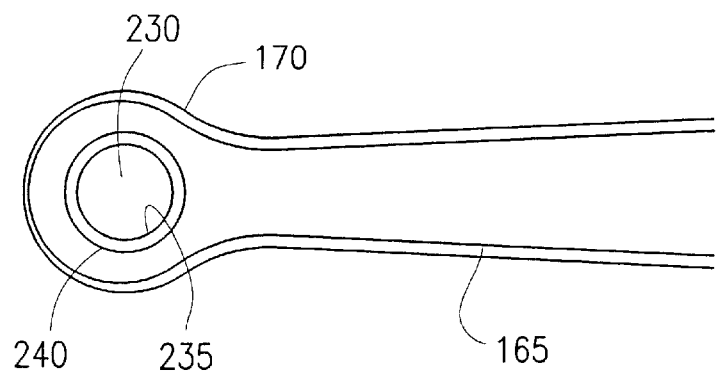
FIGS. 15–17 are views of a foot and an arm of the patellar guide of FIG. 6.
Figure 16:
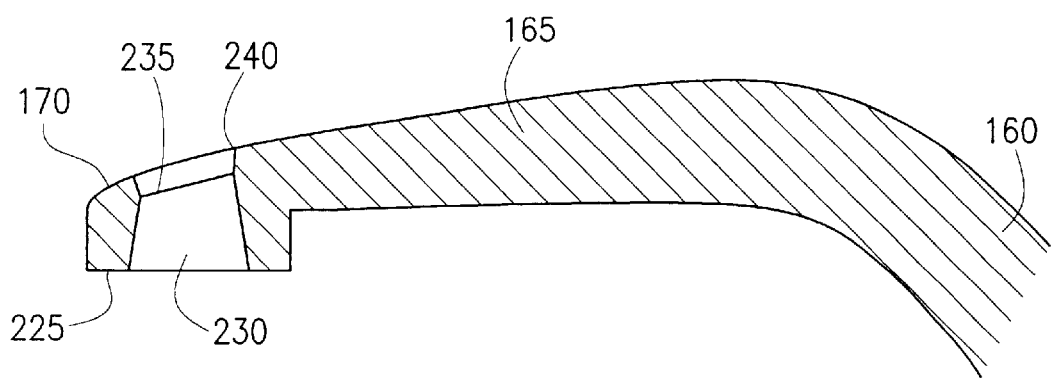
Figure 17:
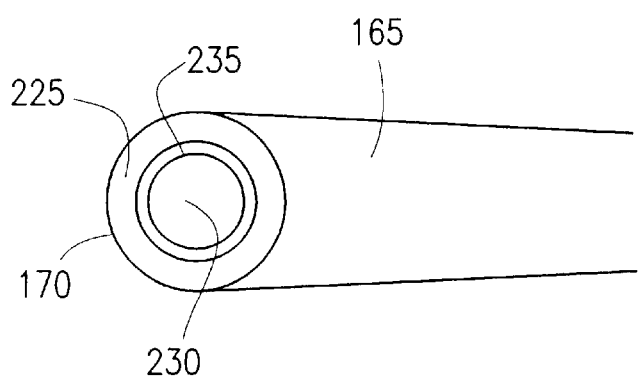

The patellar guide 105 also includes an extension 160 that connects the arm 145 to a second arm 165 (shown in detail in FIGS. 15–17). The second arm 165 is generally parallel to the arm 145, and includes a foot 170.

Figure 7:
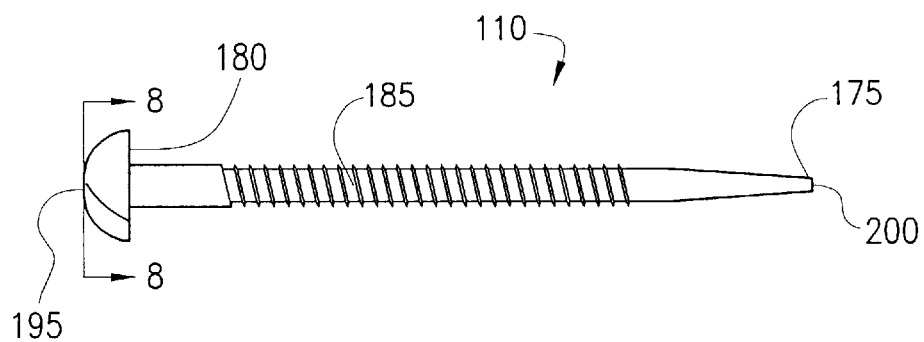
FIG. 7 is a front view of a bullet.
Figure 8:
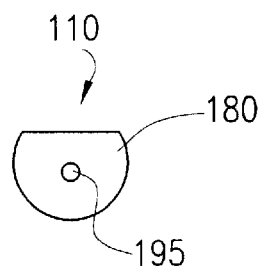
FIG. 8 is a top view of the bullet of FIG. 7 taken along section line 8—8.

To install the bullet 110 in the director handle 100, a narrow end 175 of the bullet is inserted into the channel 135 and the bullet is pushed forward. A knob 180 limits the forward movement of the bullet. The bullet 110 includes a series of equally spaced circumferential grooves 185 cut along its length (FIG. 7). When the bullet 110 is inserted into the channel 135, they interact with one or more circumferential tabs 190 to prevent forward or reverse movement of the bullet. Because the grooves 185 are not cut along the entire circumference of the bullet, turning the knob 180 so that the grooves do not face the tabs 190 allows the bullet to be pushed forward or pulled out. Bullet 110 also includes an opening 195 in the knob 180 (FIG. 8) and an opening 200 in the narrow end 175. The openings 195, 200 are at the opposite ends of a channel running through the bullet 110. The channel and openings are sized to receive the guide wire 115 to drill a hole during the repair of damaged articular cartilage.

Figure 18:
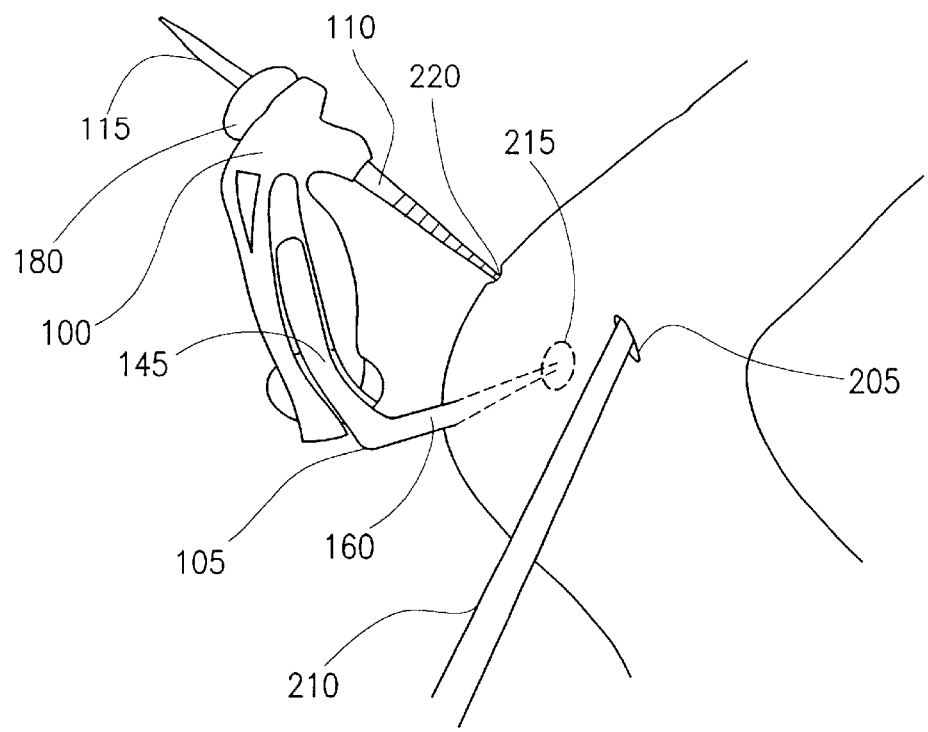
FIG. 18 is a side view of an arthroscopic surgery on the knee joint.

Referring to FIG. 18, in an arthroscopic method of using the surgical instruments to replace damaged articular cartilage 40, three incisions are made to access the knee joint 15. A first incision 205 provides access for a camera 210, which provides visualization of the interior of the knee joint 15 to the surgeon. A second incision 215 provides access for the patellar guide 105 to be placed adjacent to the posterior surface 35 of the patella 25. A third incision 220 provides access for the bullet 110. As shown in FIG. 18, the director handle 100, guide 105, bullet 110, and guide wire 115 are assembled and inserted into the knee joint 15. The patellar guide 105 is manipulated such that the second arm 165 and foot 170 are inserted into the second incision 215. Using the camera 210 inserted into first incision 205, and while viewing the posterior surface 35 of the patella 25, the surgeon manipulates the guide 105 to place the foot 170 against the damaged articulating cartilage 40 on the posterior surface 35.

Figure 19:
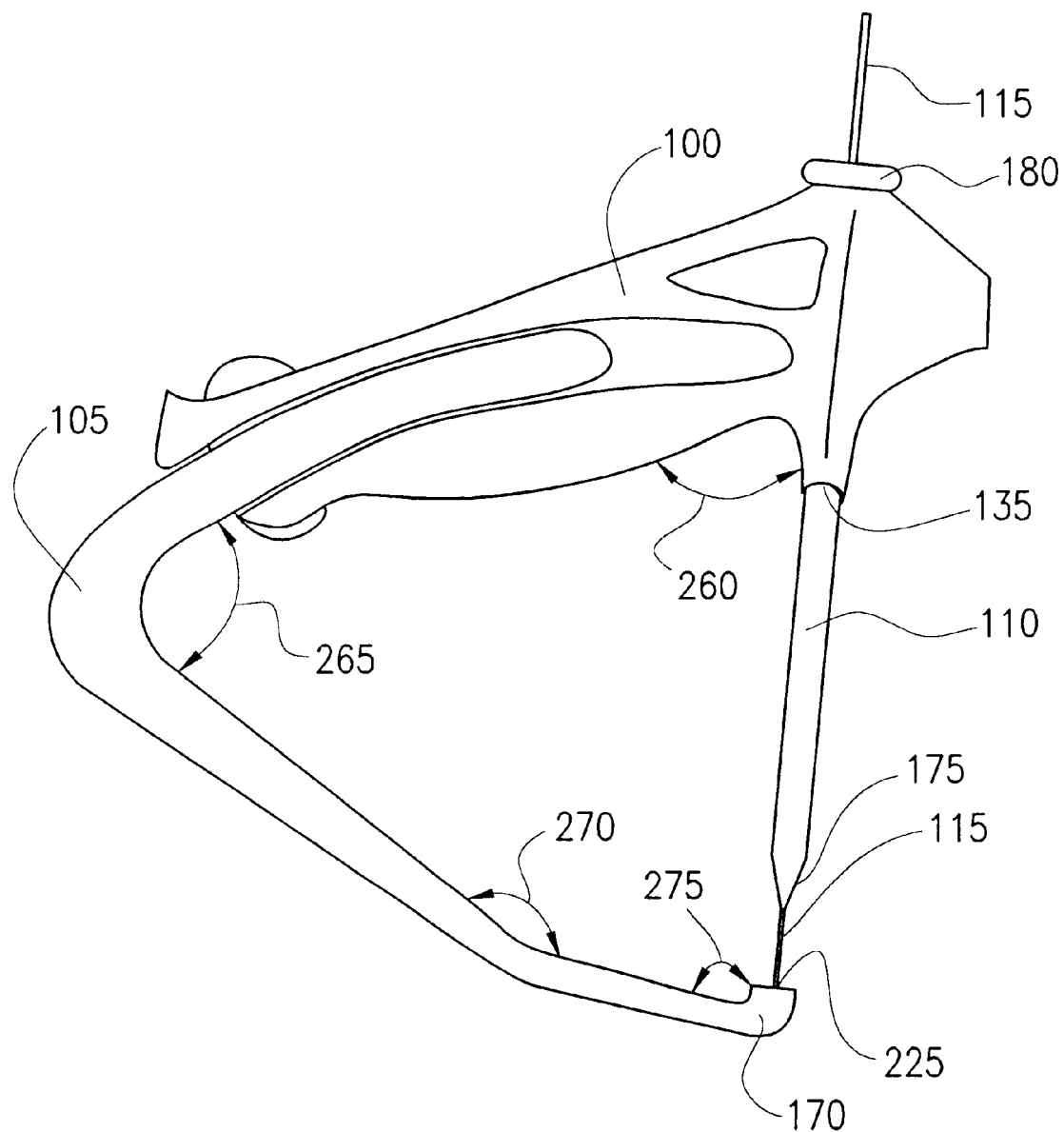
FIG. 19 is a front view of the director handle, the patellar guide, the bullet, and the guide wire.

FIG. 19 shows the assembled instrument. As shown, the foot 170 has a flat upper surface 225 that is oriented in the direction of the narrow end 175 of the bullet 110. A channel 230 passes through the foot 170, narrowing from upper surface 225 to a lip 235. The channel 230 then widens from the lip 235 to an opening 240. When the guide wire 115 is drilled into the patella 25, it enters the anterior surface 30 and exits the posterior surface 35 into channel 230. The lip 235 has a diameter that is less than the outer diameter of the guide wire 115, thereby preventing the guide wire from drilling in too deep and damaging other structures of the knee joint 15. The director handle 100, guide 105, guide foot 170, and bullet 110 are oriented so that the upper surface 225 of the foot 170 is perpendicular to the posterior surface 35 of the patella. Thus, when the guide wire 115 is used to drill a channel 245 in the patella, an opening 250 of the channel on the posterior surface will be perpendicular to the posterior surface 35.

The lip 235 is one stopping means to prevent the guide wire from drilling too deep. Other stopping means may be used to prevent the guide wire from drilling in too deep. One example of another stopping means is a hollow insert that can be inserted into the opening 230. The insert can have a perpendicular lip that protrudes into a channel of the insert, which is co-axial with the channel 230, and functions as a stop for the guide wire. A number of inserts can be made available to the surgeon such that the channel through the insert has a range of diameters. In this manner, the surgeon can choose the diameter of the guidewire based on the patient's particular anatomy and choose the appropriate insert to use with the guide and guidewire. Of course, other stopping means beyond the lip 235 and the insert may be used to prevent the guidewire from drilling in too deep.

The shape of the surface 225 may be varied, for example, to be generally round, oval, square, or of another shape. The surface 225 should be of sufficient area such that it will rest securely against the patella. The surface 225 can have an area larger or smaller than the opening 230, although the area of the surface 225 should be sufficiently large enough to form a secure and stationary contact with the patella during surgical procedures employing the guide 105. The surface 225 also can be configured to improve the contact between the guide 105 and patella. For example, the surface can be rough, knurled, or textured with protrusions of varying fineness. These types of surfaces would be configured to cause the surface 225 of the guide to rest firmly against the patella and resist lateral movement.

The orientation is created by setting the angles (260, 265, 270, 275) such that the flat surface 225 of the foot 170 is perpendicular to the longitudinal orientation of the channel 135, or of the bullet 110 and guide wire 115 inserted through it. This can be done, for example, by providing markings on the guide 105 and the director handle 100 so that aligning the markings will set the longitudinal orientation of the channel 135 perpendicular to the flat surface 225 of the foot 170. Alternatively, the surgeon can set the perpendicularity at the time of surgery by adjusting the position of the guide relative to the director handle to make the longitudinal orientation of the channel perpendicular to the flat surface of the foot. This method is aided by inserting the bullet 110 and the guide wire 115 into the channel 135, and placing the guide wire 115 in the channel 230. Although perpendicularity is desirable, a deviation from perpendicularity is acceptable. For example, a deviation from approximately 5° to 10° from perpendicular should be close enough. Greater deviations also may function adequately.

After the guide wire 115 has been used to drill the channel 245 through the patella, described with reference to FIG. 18, the guide wire is pulled back a short distance so that it is not in the channel 230 of the foot 170. The bullet 110 then is pulled back from the incision 220 and out of the channel 135 of the director handle 100, which leaves the guide wire 115 resting loosely within the channel 135. The patella guide 105 then is pulled out of incision 215 and the director handle 100. With the guide wire 115 remaining in the channel 245, the drill 120, which has a channel 280 passing through it (FIG. 11), is inserted over the guide wire 115 and used to enlarge the channel 245. The drill may have, for example, an outer diameter of 4.9 mm.

Figures 20, 21:
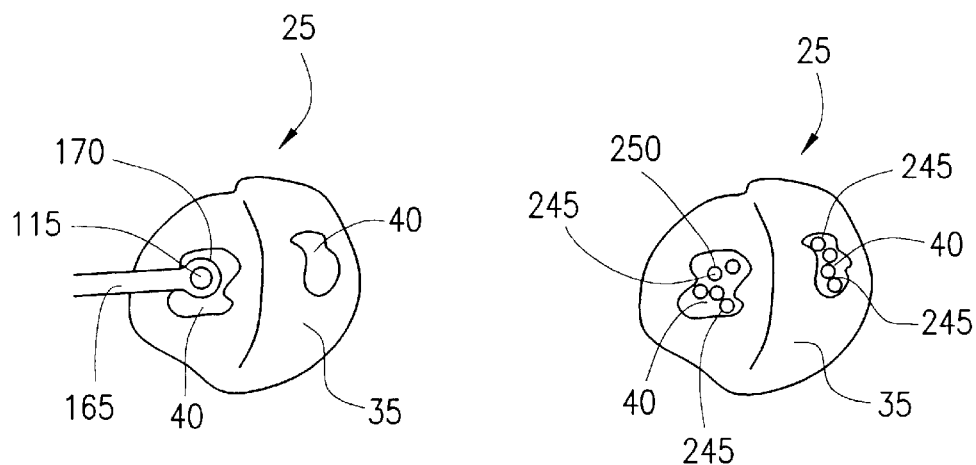
FIGS. 20 and 21 are posterior views of the patella showing areas of damaged cartilage.

One or more channels 245 can be made in the area of damaged articular cartilage 40 (FIGS. 20 and 21). The channels 245 should be located close together so that a tightly-packed matrix of healthy grafted cartilage can be implanted to cover the area 40 as completely as possible. But a sufficient wall thickness (e.g., 1 mm) should be maintained between adjacent channels to provide a stable and healthy environment for the implanted grafts.

Figure 22:
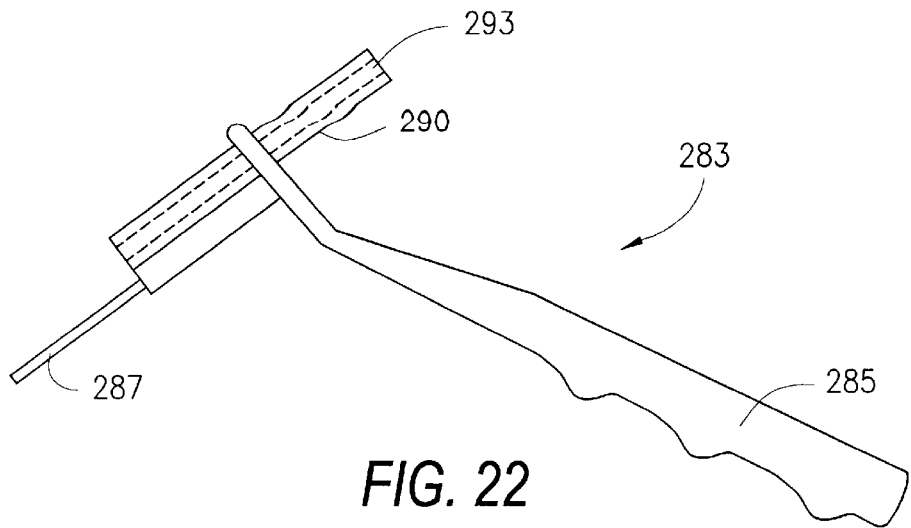
FIG. 22 is a side view of an offset tool.
Figure 24:
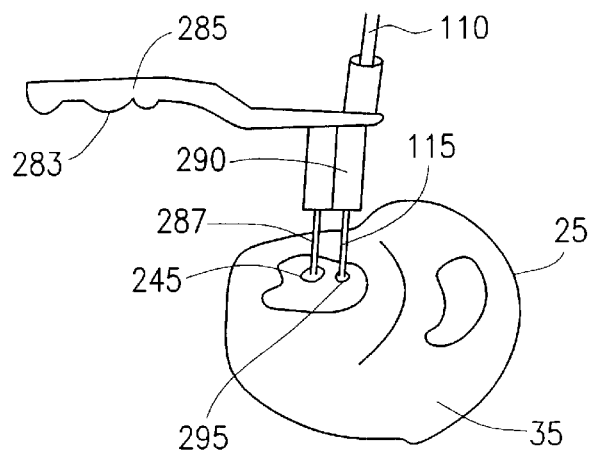
FIG. 24 is a perspective view of the offset tool of FIG. 22 aiming a guide wire on to the posterior surface of the patella.
Figure 23:
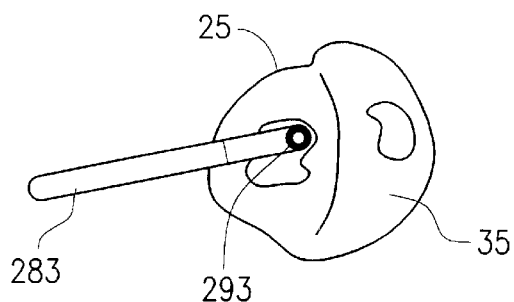
FIG. 23 is a top view of the offset tool of FIG. 22 above the posterior surface of the patella.
Figure 26:
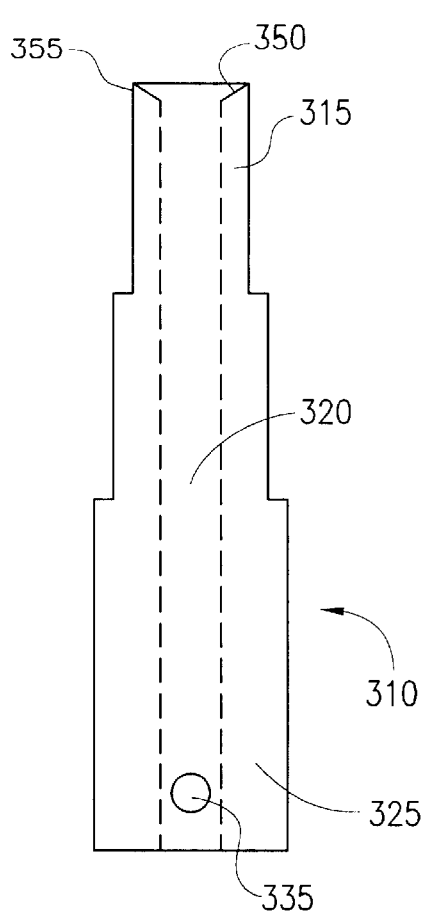
FIG. 26 is a front view of the chisel tool of FIG. 25.
Figure 27:
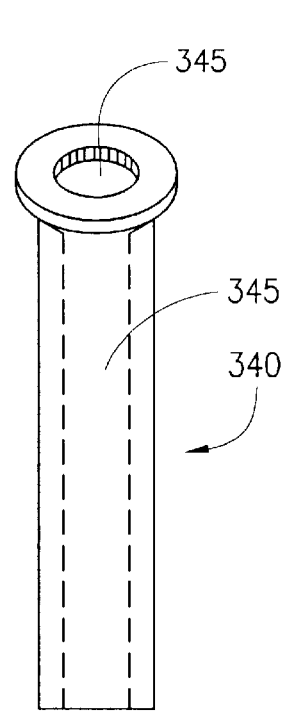
FIG. 27 is a perspective view of a chisel guard for use with the chisel tool of FIG. 25.
Figure 28:
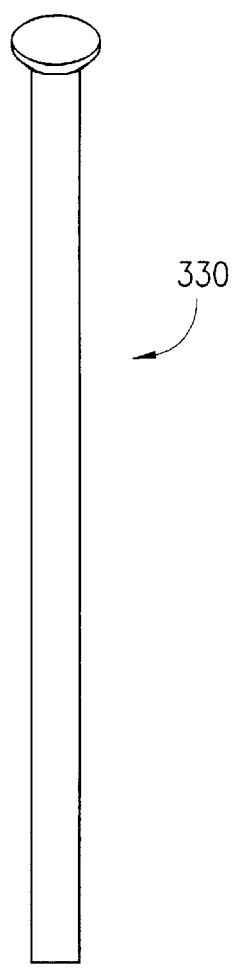
FIG. 28 is a perspective view of a tamp for use with the chisel tool of FIG. 25.
Figure 25:
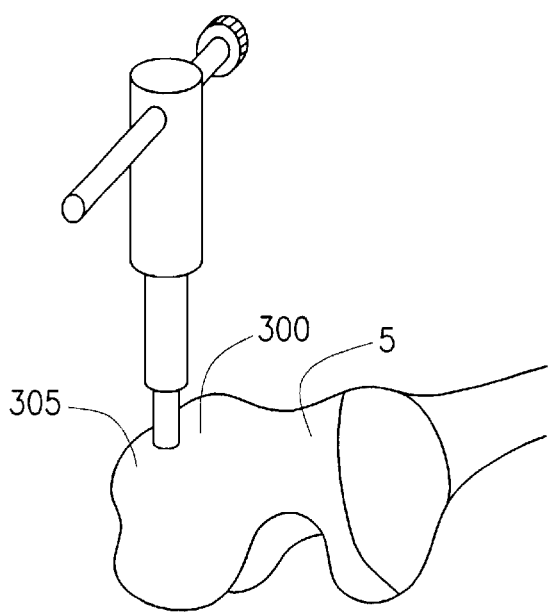
FIG. 25 is a perspective view of a chisel tool harvesting a cartilage graft.
Figure 29:
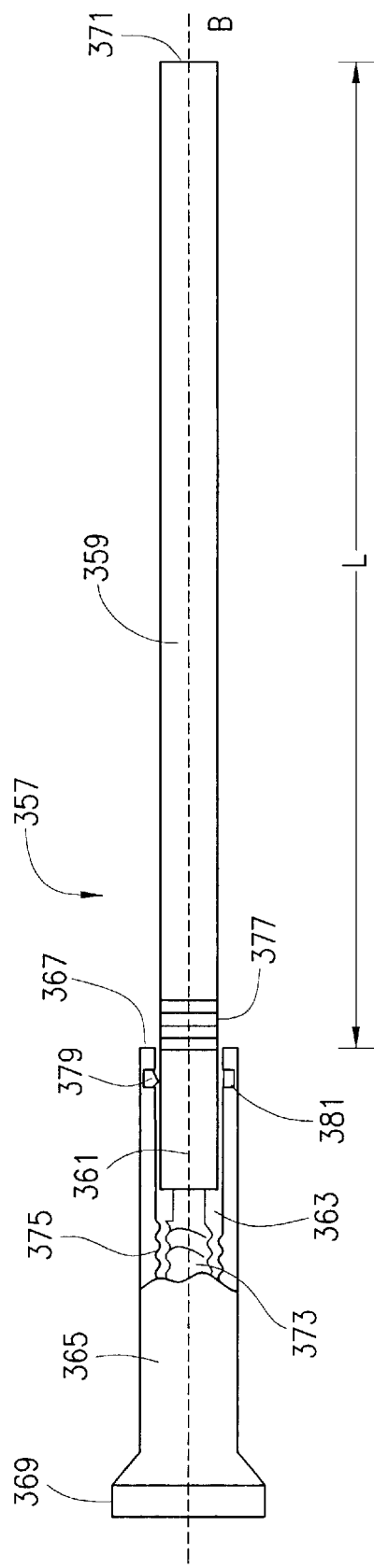
FIG. 29 is a partial cross-sectional side view of an insertion tool.

Referring to FIGS. 22–24, an offset tool 283 includes a handle 285, an offsetting probe 287, and a guide 290 having an inner shaft 293. The offset tool 283 is configured such that the longitudinal axis of the inner shaft 293 is offset by approximately 2 mm–3 mm from the offset probe 287. The offset probe 287 may be a pin inserted into a channel such that it can be moved and replaced with other pins of different lengths. To drill offset channels adjacent to channel 245, the offsetting probe 287 is inserted through incision 220 into existing channel 245. Then, with the director handle 110, patella guide 105 and bullet 110 assembled, patella guide 105 is placed against the posterior surface 35 of the patella and the bullet 110 is inserted into the inner shaft 293. The guide wire 115 then is used to drill a channel 295 that is offset from channel 245. Because the flat surface 225 of the foot 170 is flush with the posterior surface 35 of the patella, the channel 295 will be approximately perpendicular to the posterior surface 35.

Referring to FIGS. 25–28, after creating channels 245 and 295, a chisel 310 is used to harvest healthy cartilage from a donor site 300 located, for example, at the ipsilateral side of the nonarticular condylar surface 305 of the femur 5. The chisel 310 is inserted into the patient's knee joint 15 so that a chisel tip 315 engages the surface of the donor site 300. The surgeon gently rocks the chisel 310 back and forth on the surface 300 until he or she feels that the chisel tip 315 is flush with the surface. With the chisel tip 315 in this orientation, the chisel shaft 320 is approximately perpendicular to the cartilage surface at donor site 300. Although a perpendicular orientation is desirable, deviations of approximately 5° to 10° and more may be acceptable.

With the chisel 310 aligned perpendicularly to the surface of donor site 300, the surgeon taps or pounds chisel handle 325 with a hammer (not shown) to drive chisel tip 315 into the bone beneath donor site 300 to a depth of approximately 15 mm–20 mm. After the chisel 310 is fully seated, the surgeon inserts tamp 330 transversely through a hole 335 in the chisel handle 325 to form a "T" shaped tool, which provides the surgeon with increased leverage when chiseling a graft. The surgeon moves the tool back and forth until the graft breaks away from the underlying bone.

The graft is removed from the condylar surface by pulling the chisel 310 away from the donor site. The chisel 310 then is pulled straight up and out of the patient's knee joint 15. The tapered interior 350 of the chisel tip 315 holds the graft within the tip as the instrument is withdrawn. The chisel guard 340 also protects the surgeon from being cut by the chisel.

The graft is primarily bone tissue having a proximal end covered by a layer of hyaline cartilage. The graft is removed from the chisel 310 by sliding chisel guard 340 over chisel tip 315, inserting tamp 330 into the chisel's distal end 355, and pushing against the bony end of the graft to slide the graft through the chisel shaft 320 and out of the proximal end of handle 325. Removing the graft in this manner avoids the need to push against the hyaline cartilage (i.e., as would be done by inserting the tamp 330 into the handle 325 rather than into the tip 315), thereby reducing the risk of damaging the hyaline cartilage. This is particularly important because the graft often is tightly wedged within tip 315 due to the large forces applied during chiseling. After the graft is removed from the chisel 310, the graft may be cut to the desired length (e.g., 15 mm–25 mm).

To transplant the harvested graft, the graft is inserted cartilage end first through incision 220 into the channel 245 in the patella. The graft is inserted into the channel on the anterior side 30 of the patella and tamped until the cartilage end is flush with the cartilage on the posterior surface 35 of the patella, as viewed through arthroscopic camera 210.

The graft can be inserted by hand or, with reference to FIGS. 29–33, by inserting the graft using an insertion tool 357. The insertion tool 357 includes an axially elongated cylindrical metal rod 359 having a proximal end 361 that is received within a chamber 363 in a handle 365 to allow adjustment of a length L of the rod 359 that protrudes from a distal end 367 of the handle 365. A proximal end 369 of the handle 365 has an enlarged shape to enable the surgeon to securely grasp the handle 365 while adjusting the length L.

The rod 359 is sized to fit within a drill guide 370 and has a flat distal end 371 oriented perpendicularly to a rod axis B. The proximal portion 361 of the rod 359 has a threaded portion 373, which corresponds with a threaded portion 375 of the handle 365. Calibration markings 377 are disposed on the rod 359 distal of the proximal portion 361. The markings 377 are spaced 1 mm apart and may be designated by numerals (e.g., 0, 1, 2).

The configuration of the chamber 363 is substantially complementary to that of the portion of the rod 359 that fits within the handle 365. That is, the chamber 363 includes the threaded portion 375 that receives the threaded portion 373 of the rod 359. An O-ring 379 is disposed in a groove 381 formed around the exterior of the chamber 363 slightly proximally of handle end 367.

Figure 30:
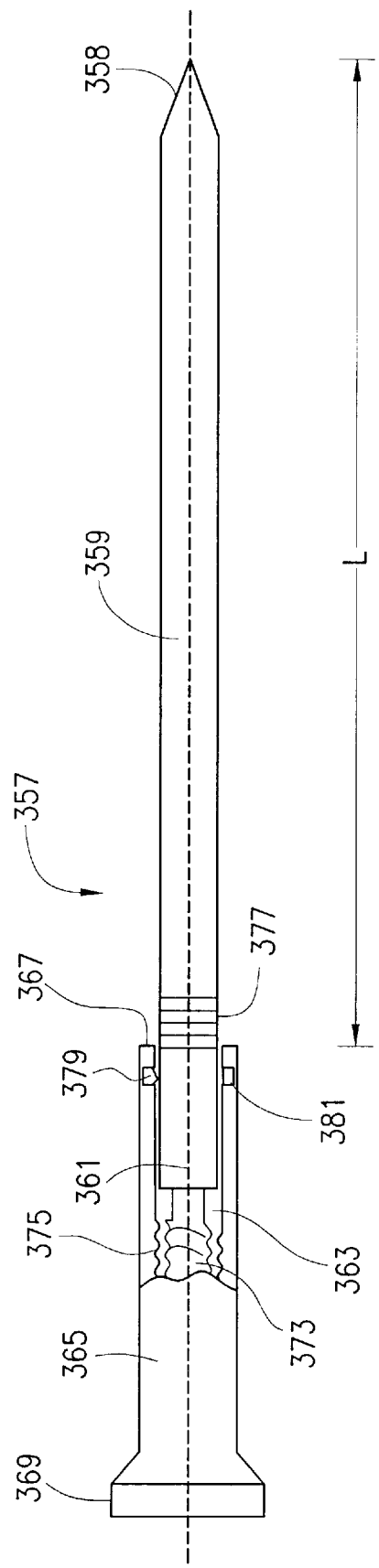
FIG. 30 is a partial cross-sectional side view of the insertion tool of FIG. 29 having a pointed end for forming a divot.
Figure 31:
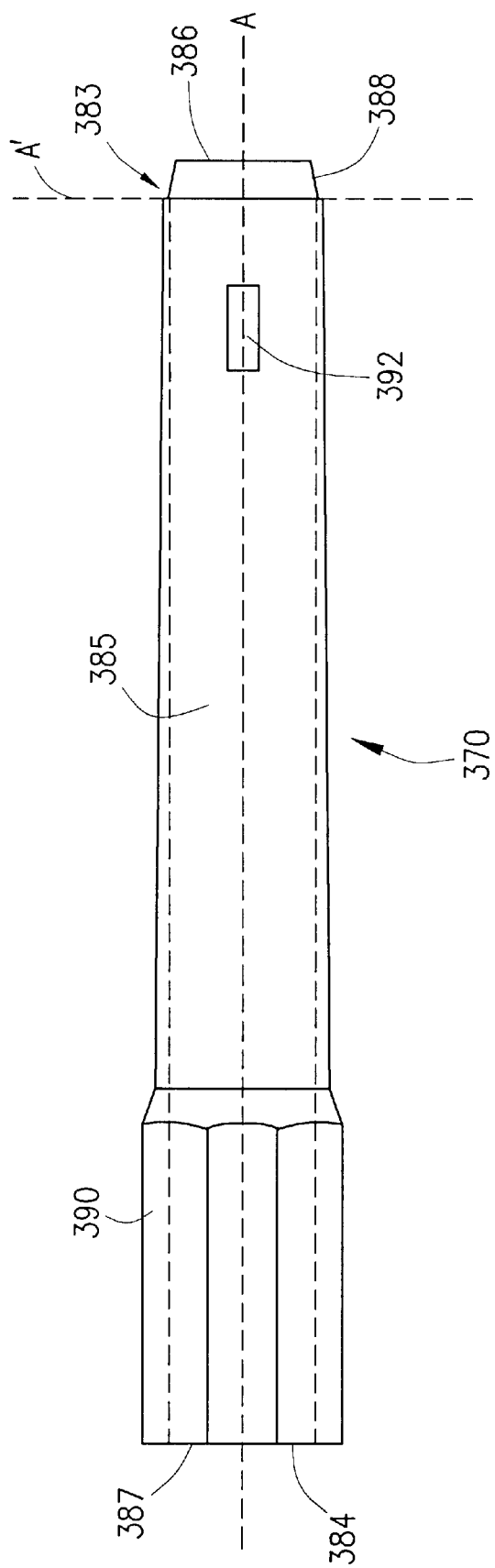
FIG. 31 is a side view of a drill guide.
Figure 32:
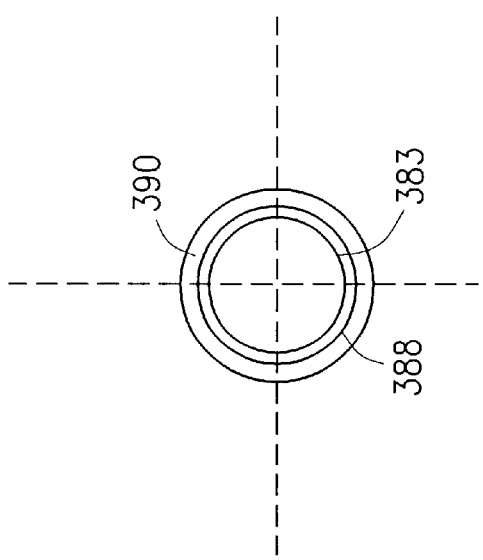
FIG. 32 is a top view of the drill guide of FIG. 31.

The surgeon adjusts the length L of the rod 359 by rotating the rod with respect to the handle 365 (e.g., by twisting the rod 359 further into the handle 365) while observing the calibration markings 377. The friction between the O-ring 379 and the rod 359 helps to hold the rod in place within the handle at the position set by the surgeon. The markings 377 indicate the length of the rod 359 protruding from the handle 365, and more specifically identify the spacing between the rod's distal end 371 and a tissue-engaging rim 383 of the drill guide 370 (FIGS. 31 and 32). For example, when the marking 377 designated by numeral 0 is aligned with the handle's distal end 367, the length L of the rod 359 equals that of the guide 370 to the rim 383, and as a result the rod's distal end 371 is flush with the rim 383 when the insertion tool 357 is fully inserted into the drill guide 370 (with the distal end 367 of the handle 365 abutting the guide's proximal end 384). As illustrated in FIG. 30, the rod 359 may have a pointed end 358, which is used to form a divot in a graft to expand the graft to fill in the diameter of the channel in which the graft is placed.

Referring to FIGS. 31 and 32, the drill guide 370 includes an interior passage 385 that extends between an open distal end 386 and an open proximal end 387. The drill guide 370 is elongated along a longitudinal axis A. The rim 383 and a flange 388 are at the distal end 386 such that when the drill guide 370 is positioned on a bone surface, the flange 388 contacts and is flush with the bone completely around its circumference, such that the axis A is perpendicular to the bone surface. The flange 388 helps to hold the position of the drill guide 370 perpendicular to the bone surface when the insertion tool 357 is used to insert a graft into the drilled channel 245. The interior passage 385 is sized and shaped to receive the insertion tool 357, which in turn is dimensioned according to the desired diameter of the graft.

The drill guide also includes a handle 390 at the proximal end 387. The handle has an outer diameter larger than the remainder of the drill guide 370 to ease gripping of the drill guide. Because the diameter of the interior passage 385 is constant, the proximal end 387 is thicker and able to withstand the impact of instruments, such as the insertion tool 357. A window 392 is formed in the wall of the tool near the distal end and is open to the interior passage 385. The window 392 allows the surgeon to see into the passage 385 during use to visualize the position of the graft during its delivery.

Inserting the rod 359 farther into the handle 365 causes the rod's distal end 371 to be recessed from the rim 383 by a distance that corresponds to the calibration marking 377 (e.g., 1 mm, 2 mm, 3 mm) that is aligned with the handle's distal end 367. For example, when the length L of the rod 359 is set at the marking designated by the numeral 3, the distal end 371 of the rod 359 is recessed by 3 mm from the rim 383 of the drill guide 370. This enables the surgeon to insert the graft at a precise depth in the graft receiving hole so that the cartilage on the graft protrudes from the hole by an amount that corresponds to the height of the surrounding cartilage.

Figure 33:
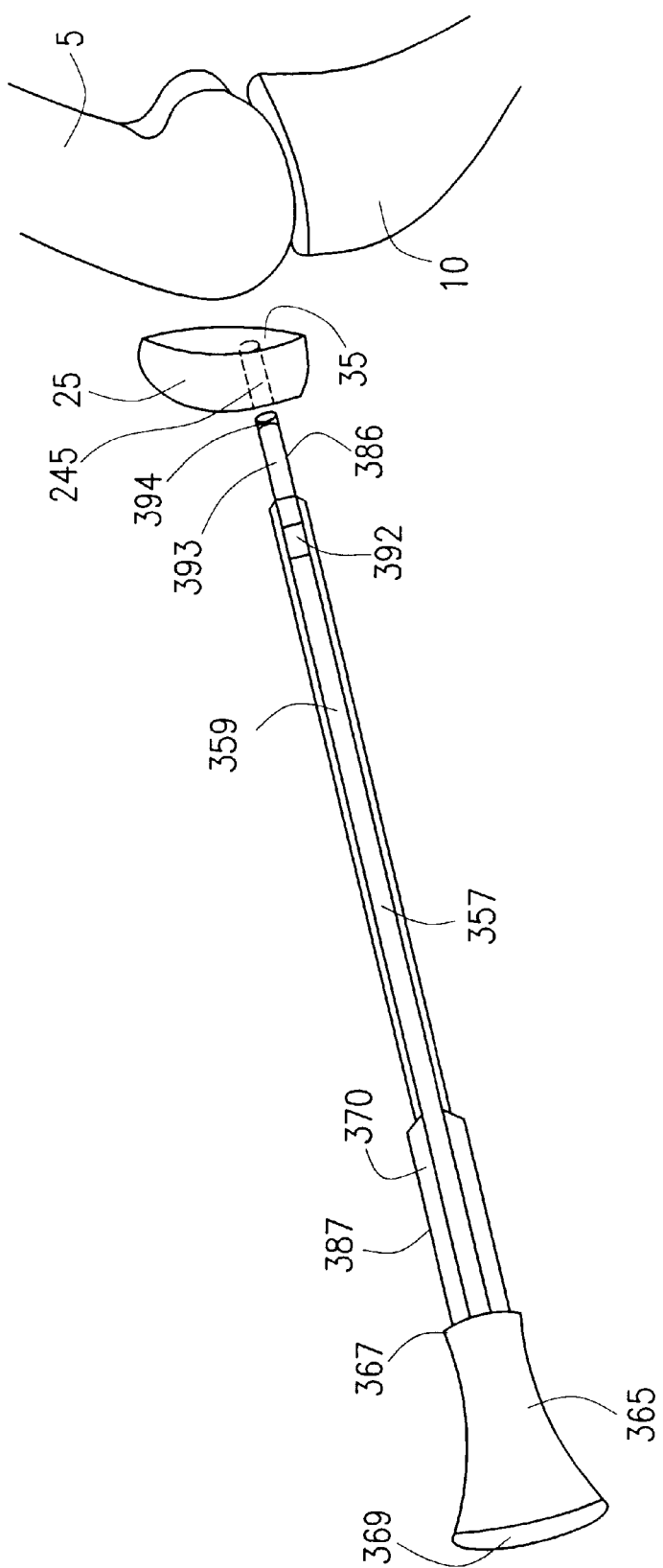
FIG. 33 is a perspective view showing the use of the insertion tool and the drill guide to deliver a graft in the patella.

As shown in FIG. 33, the graft 393 is implanted at the desired depth in the channel 245 by advancing the insertion tool 357 into the guide 370 until the distal end 367 of the handle 365 abuts the proximal end 387 of the drill guide 370. Thus, the rod 359 pushes a graft 393 out of the distal end 386 of the drill guide 370 and positions the graft 393 at the desired depth in the channel 245 such that the layer of hyaline cartilage 394 on the graft 393 is flush with the layer of articular cartilage that surrounds the channel 245 on the posterior surface 35 of the patella 25. This process is repeated until all of the harvested grafts 393 are implanted into the channels 245.

If the graft is too short for the channel 245, another bone plug is sized and used to fill in the remainder of the channel. To size the bone plug, it is inserted into tapered bone plug compressor 125 (FIGS. 12–14) and then extruded through a tapered channel 395 so that it forms a compacted, precise outer diameter plug. The plug is removed from the compressor 125 and inserted into the channel 245. Because the plug has an exact outer diameter, it forms a tight interference fit in the channel 245 to prevent the graft from coming out of the anterior surface 30 of the patella. Any excess plug is trimmed away from the anterior surface 30.

If a bone plug of suitable diameter is not available to size through the compressor 125, a bone plug may be inserted into the channel 245 and the rod 357 with the pointed end 358 placed against the bone plug. By pressing the pointed end 358 against the bone plug with sufficient force to form a divot, the bone plug will expand to fill the diameter of the channel 245 to form a cap.

Figure 34:
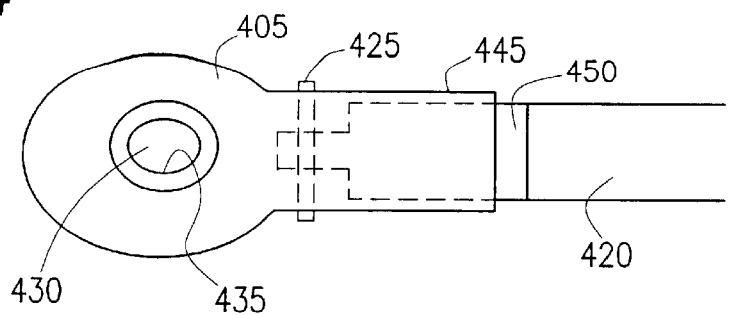
FIG. 34 is a front view of a patellar guide having a movable foot.
Figure 35:
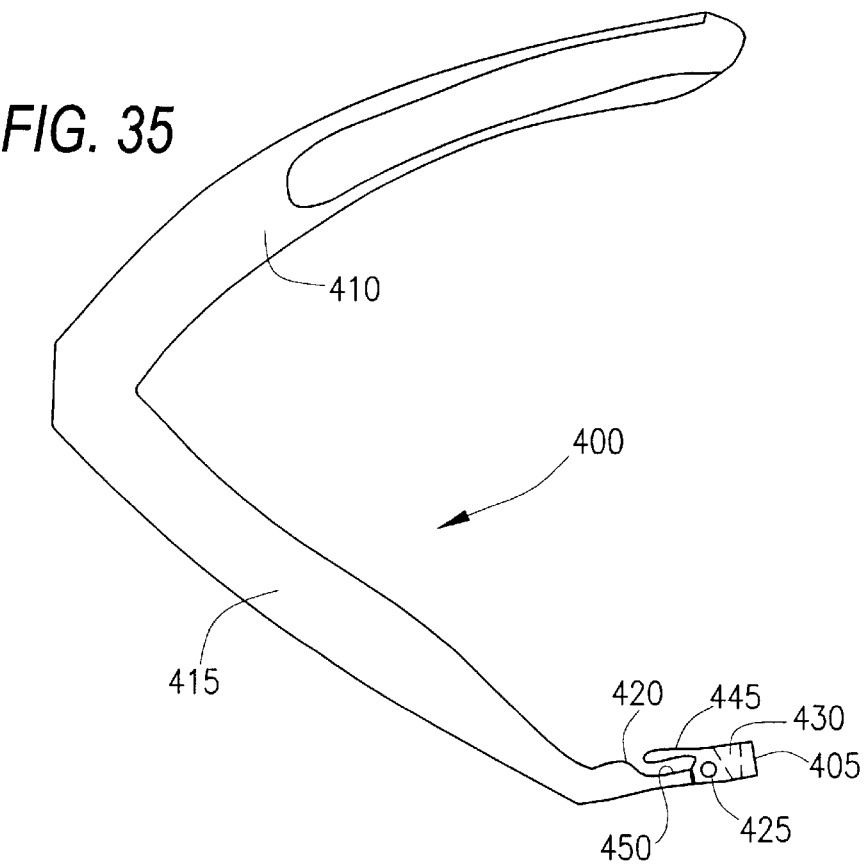
FIGS. 35 and 36 are top and front views, respectively, of the movable foot of FIG. 34.
Figure 36:
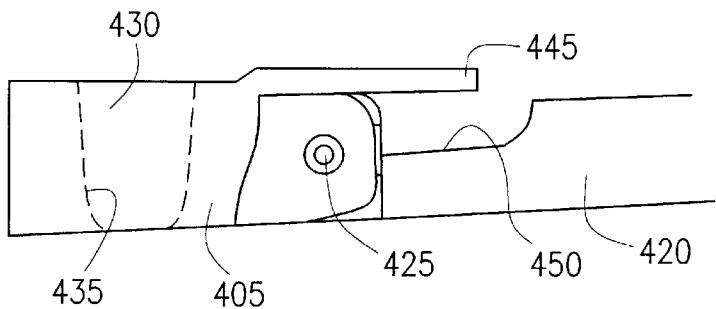

Referring to FIGS. 34–36, a patella guide 400 may include a pivotal foot 405, an arm 410, an extension 415, and a second arm 420, to which pivotal foot 405 is pivotably attached by a pin 425. Like foot 170, the foot 405 includes a tapered shaft 430 into which a guide wire can drill but is prevented from passing through because of a taper 435. The patella guide 400 is used in a manner similar to that of patella guide 105 except that pivotal foot 405 will pivot to be flat against any surface and not necessarily provide a perpendicular relationship between a channel drilled through the patella and the posterior surface 35 of the patella. The pivotal foot 405 includes an extension 445 which functions as a stop when the foot 405 pivots. A cut-out segment 450 of the second arm 420 has a cut-out length that is longer than the extension and will accept the extension when the foot pivots. The cut-out segment 450 can be cut to a deep or shallow length depending on the amount of pivoting acceptable.

Figure 37:
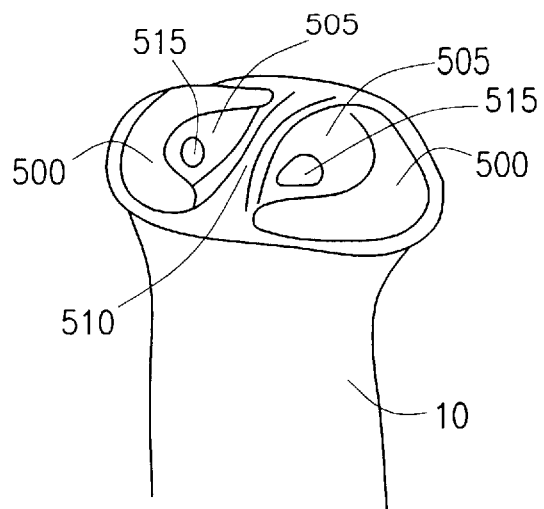
FIG. 37 is a top perspective view of the tibia showing the tibial plateau.

Other articular surfaces of the knee joint 15 may become damaged or worn and need repair. For example, referring to FIG. 37, the tibia 10 has articulating surfaces that include a pair of menisci 500 and a pair of articular cartilage surfaces 505, each pair being separated by a tibial plateau 510. The femoral condyles 17 (FIG. 1) articulate against the articular cartilage surfaces 505 and the menisci 500. The articular cartilage surfaces 505 can become damaged or worn due to the constant wear or mechanical shocks.

An arthroscopic method for replacing damaged or defective cartilage, such as on one or more areas 515 of damaged articular cartilage on the articular cartilage surfaces 505, includes using specialized tools to drill an oblique channel for a recipient graft and to place the recipient graft. The method and tools ensure that the surface of the recipient graft is flush with the articular cartilage surfaces 505 of the tibia 10.

FIGS. 38–44 show various views of a specialized set of surgical instruments for repairing the areas of damaged articular cartilage surfaces 505 of the tibia 10. The surgical instruments include a tibial guide 520, a plug holder 525, and an angled chisel 530. The surgical instruments 520, 525 and 530 are used in conjunction with the director handle 100, the bullet 110, the guide wire 115, and the drill 120.

Figure 38:
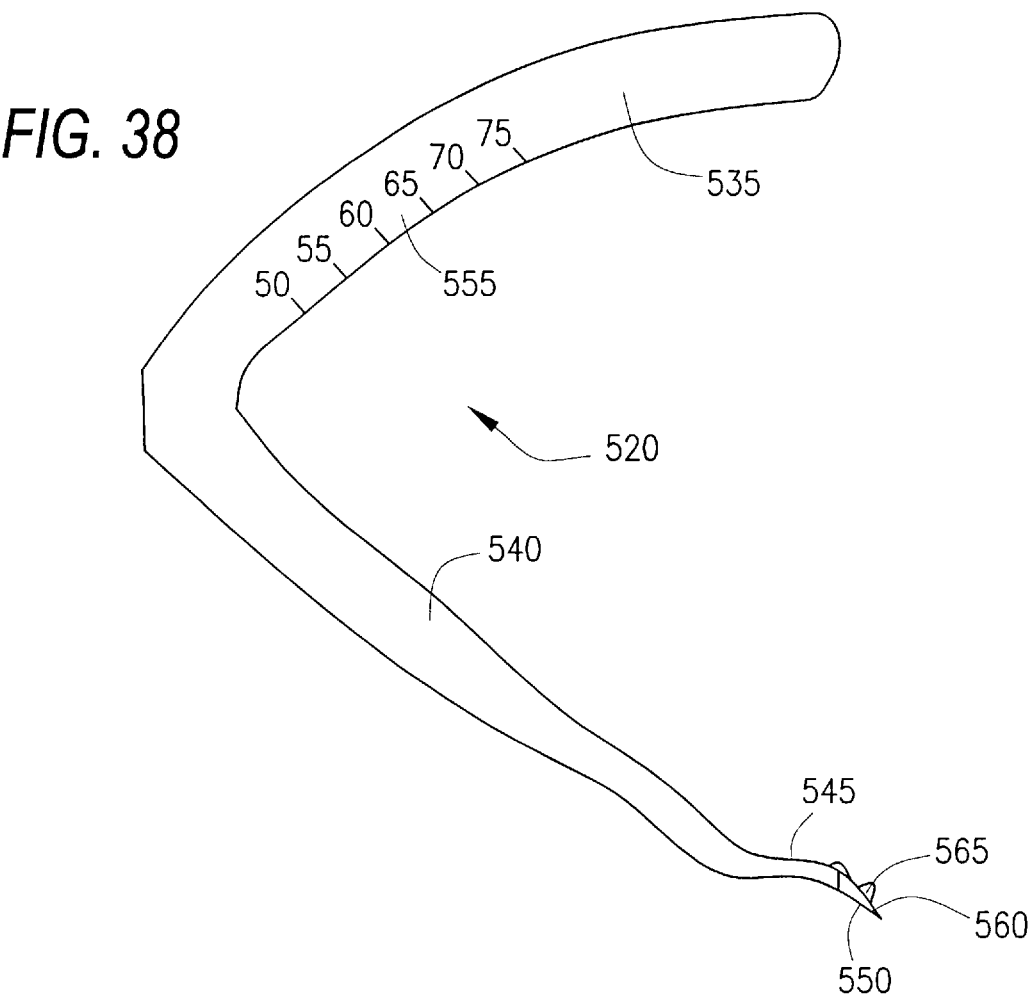
FIG. 38 is a front view of a tibial guide.
Figure 39:
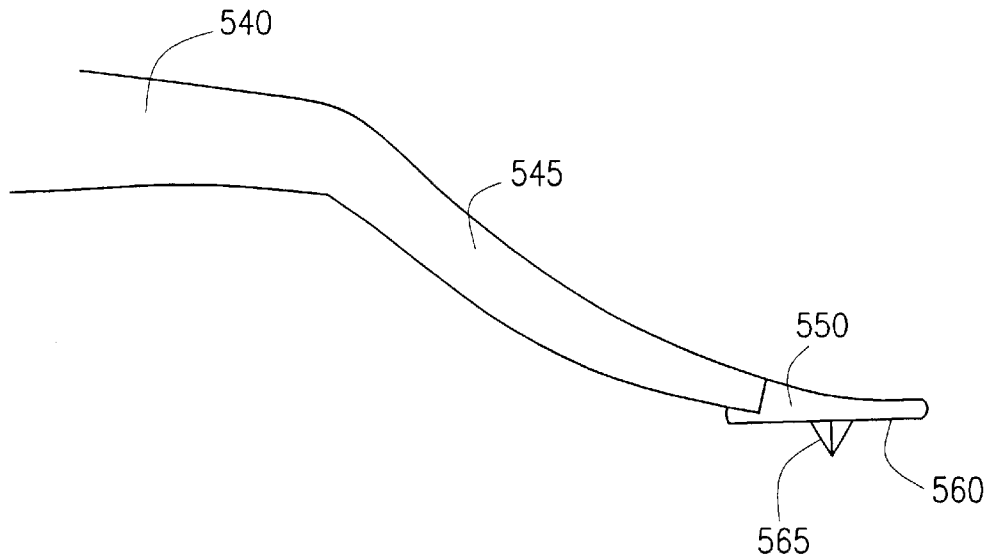
FIGS. 39 and 40 are views of a foot of the tibial guide of FIG. 38.
Figure 40:
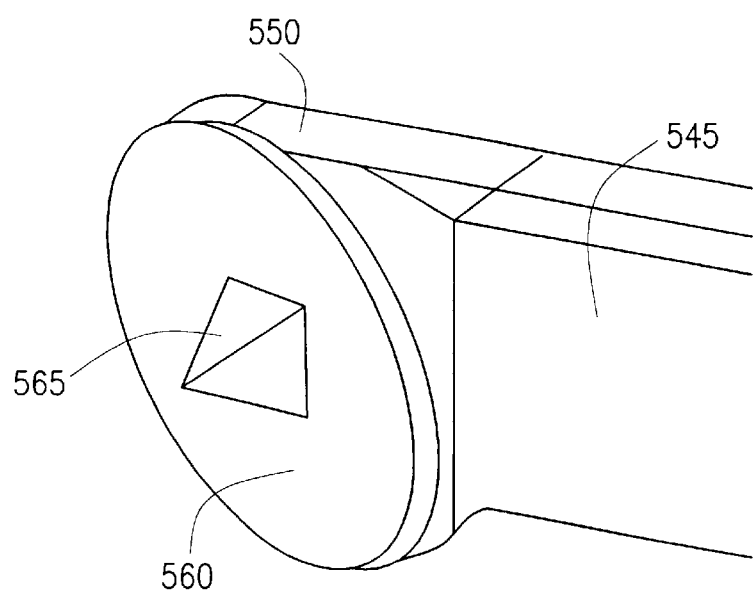
Figure 41:
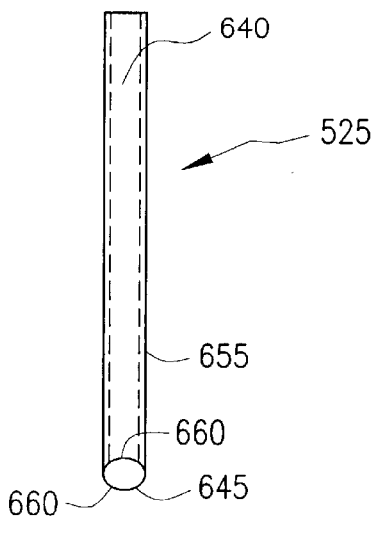
FIGS. 41 and 42 are front views of a plug holder for implanting a graft in the tibia.
Figure 42:
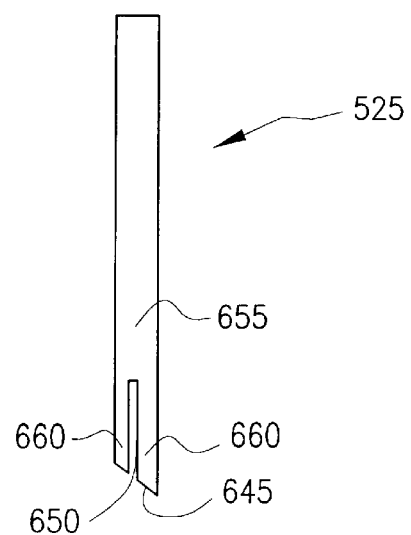
Figure 43:
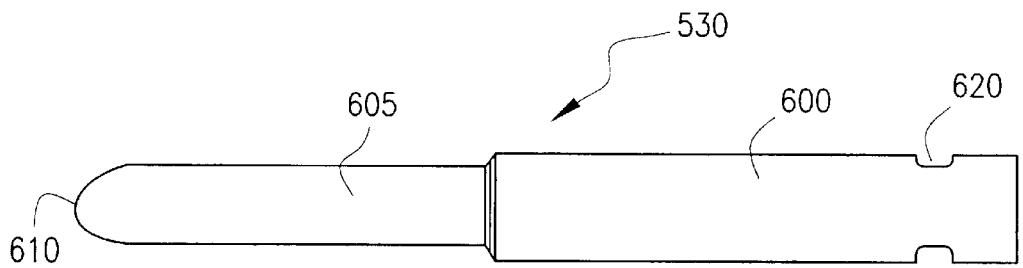
FIGS. 43 and 44 are front and cross-sectional front views of an angled chisel.
Figure 44:
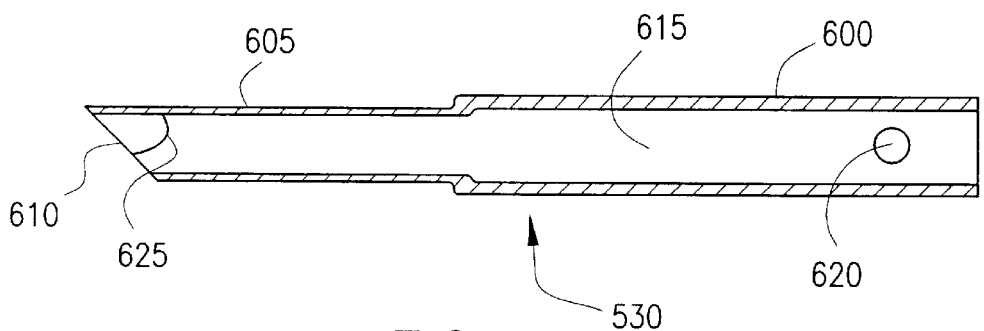

Referring specifically to FIGS. 38–40, the tibial guide 520 includes an arm 535, an extension 540, a second arm 545, and a foot 550. The arm 535 includes a scale 555 that has a series of equally spaced markings corresponding to angles to aid the surgeon in setting the angle of the guide relative to the director handle 100 when the guide is installed in the handle. The foot 550 includes a flat surface 560 from which a pin 565 protrudes. Although not shown here, the foot also may have a channel through it. The tibial guide 520 is configured so that the flat surface 560 of the foot 550 can be passed above or below the meniscus 500 and seated against the tibial plateau 510 with the pin 565 preventing the foot 550 from moving relative to the flat surface 560 when the pin is seated. To ensure that the pin 565 does not damage the meniscus and can be passed above the meniscus, the second arm 545 has a curvature that permits the surgeon to keep the pin elevated above the meniscus by sliding the second arm 545 against the femoral condyles 17 until the pin can be depressed against the tibial plateau 510. The curvature of the second arm 545 also is such that the foot 550 can be used to lift the meniscus so that it can be passed below the meniscus and the pin 565 can be placed on the tibial plateau 510. The curvature of the second arm 545 is such that it provides even pressure against the meniscus so that it is not damaged by the arm 545 by, for example, creating a point of excessive pressure that can pinch the meniscus.

Figure 45:
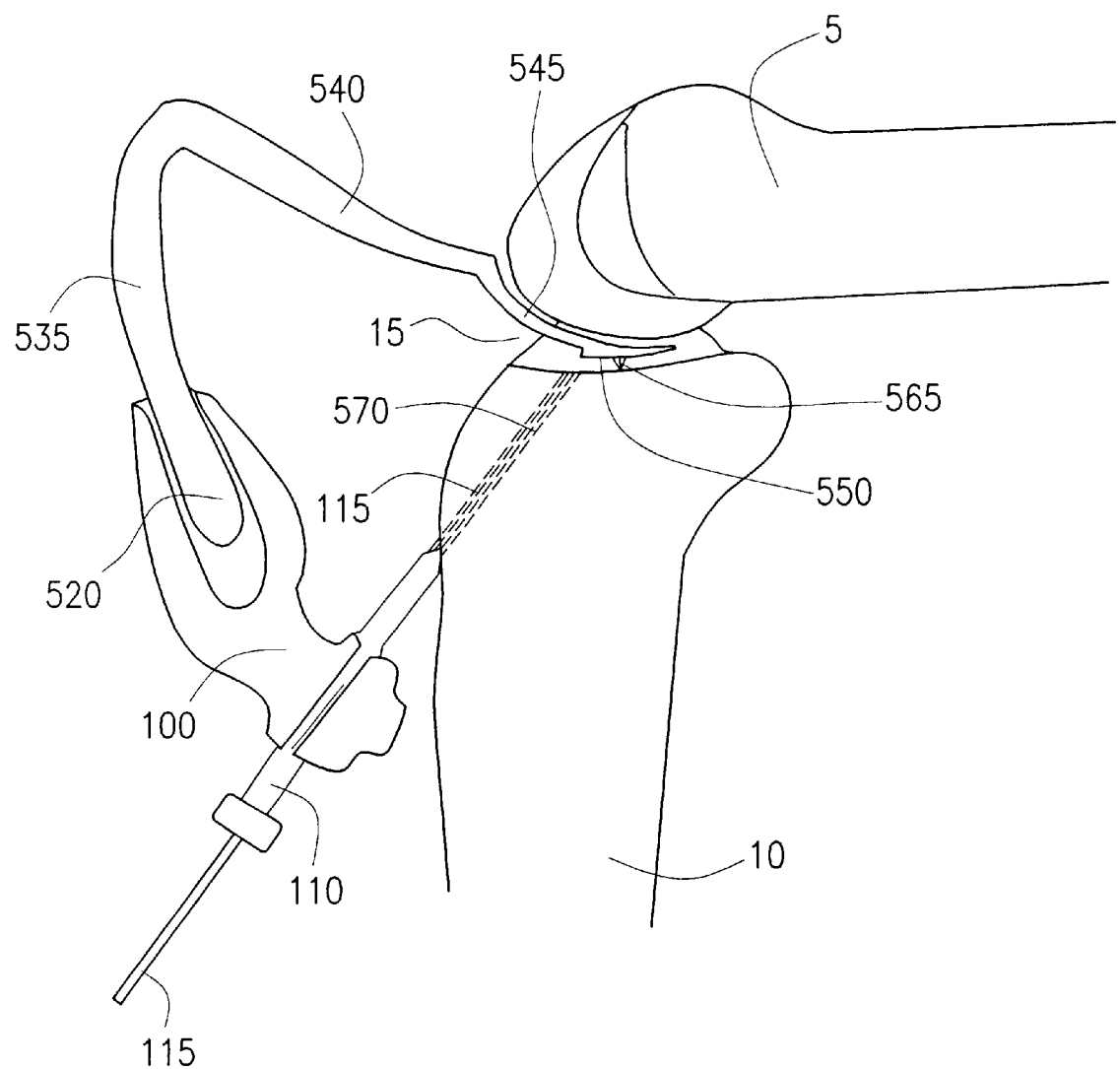
FIG. 45 is a side view of an arthroscopic surgery on a tibial surface in the knee joint.
Figure 46:
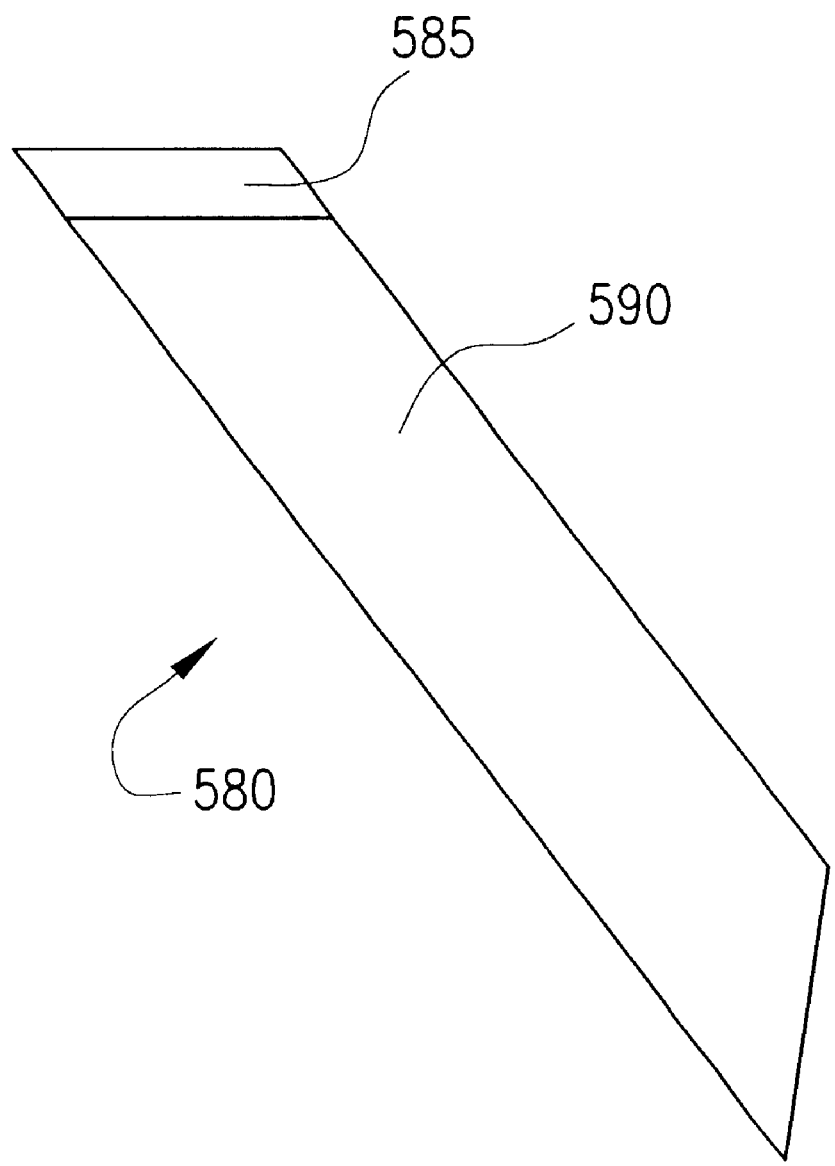
FIG. 46 is a front view of an angled graft for implantation in the surgery of FIG. 45.

Referring to FIG. 45, in using the surgical instruments, the tibial guide 520 and the bullet 110 are installed in the director handle 100, and the guide wire 115 is inserted into the bullet 110. Like the preparation of the patella for receiving a cartilage graft (FIG. 18), the guide 520, guide wire 115, and a camera (not shown) are inserted through three incisions. The guide wire is used to drill a channel 570 in the tibial shaft region of the tibia, i.e., generally the long bone portion of the tibia, up to the areas of damaged articular cartilage surfaces 505, which is adjacent to the tibial plateau 510 on which the flat surface 560 of the foot rests. The channel 570 is at an oblique angle, such as an angle of approximately 30° to the surface of the articular cartilage surfaces 505. In this manner, referring to FIG. 46, an articular cartilage graft 580 that also is harvested at an oblique angle of approximately 30° to its surface will have a cartilage surface 585 that forms a flush surface when implanted in channel 570. The graft 580 also includes a bone portion 590.

Once the channel 570 is made in the tibia, the bullet 110 and the tibial guide 520 are withdrawn from the knee joint 15 and the director handle 100, which leaves the guide wire 115 and the camera in the knee joint. The drill 120 then is placed over the guide wire 115 and used to enlarge the channel 570 in preparation for receiving a cartilage graft. Typically, more than one channel will be necessary to make a complete repair of the articular surface. Like the formation of addition channels 295 when repairing the patella's articular surface (FIGS. 23 and 24), the offset tool 283 can be used to create channels offset from channel 570. Because of the depth of channel 570, the offsetting probe 287 may be modified by using a pin longer than is necessary in the repair of the patella.

The cartilage graft 580 typically is harvested from a non-weight-bearing articular surface of the femur 5, as described above with respect to the repair of the patella 25. To ensure that the cartilage surface 585 of the graft 580 forms an oblique angle of 30° with the damaged area 515 in which it is to be transplanted, the cartilage graft is harvested using angled chisel 530. The angled chisel includes a handle 600, a tip 605, a blade 610 at the end of the tip, and a shaft 615 along its central axis. The handle includes a pair of openings 620 into which a tool, such as tamp 330 (FIG. 28), can be inserted to apply leverage to the angled chisel 530 during its use. The blade forms an angle 625 of approximately 30° with its central axis. To harvest a graft 580, the chisel 530 is placed against an articulating surface and rocked back and forth to cut through the cartilage and into the underlying bone. By inserting the tamp 330 into the openings 620 in the handle 600, additional leverage is provided to make the cut into the bone. The chisel 530 is continued into the bone until a graft of sufficient length is contained within the shaft 615.

The graft 580 is removed from the chisel 600 by removing the tamp 330 from the openings 620 and inserting the tamp into the chisel 600 at the blade 610 and pushing against the bone portion 590 so as not to damage the cartilage surface 585. The graft 580 then can be inserted into the channel 570 in the tibial shaft until the cartilage surface 585 is flush with the surface of damaged cartilage area 515. If the graft does not entirely fill the channel 570, an additional graft of bone can be taken, inserted into the tapered bone plug compressor 125 (FIGS. 12–14) and then extruded through the tapered channel 395 so that it forms a compacted, precise outer diameter plug. The plug is removed from the compressor 125 and inserted into the channel 570. Because the plug has an exact outer diameter, it forms a tight interference fit in the channel and prevents the graft 580 from coming out of the entrance of the channel in the tibial shaft region of the tibia 10. Any excess plug is trimmed away from the entrance. A bone plug also can be placed in the channel and expanded using the pointed end 358 of the rod 359 (FIG. 30) to form a divot that will fill the channel 570. Because the angle 625 of the central axis of the chisel 530 is approximately the same as the angle formed between the channel 570 and the damaged articulating surface 515, the graft 580 fits within the channel 570 such that cartilage surface 585 is flush with surface 515.

The graft 580 also can be placed in the channel 570 by using the plug holder 525. The plug holder 525 includes a shaft 640 running along its central longitudinal axis. The shaft ends at a distal angled opening 645 that has an oblique angle of approximately 30° and a pair of slots 650 cutting through the wall 655 of the holder 525 for a short distance. The slots 650 form a pair of fingers 660 that are stiff enough to hold the graft 580 but flexible enough so that they will release the graft when it is pushed out of the holder, for example, by using the tamp 330, into position in the channel 570.

In general, the tibial guide 520 and the director handle 100 are configured to be able to place the foot flush against the tibial plateau 510 and form a known angle between the longitudinal axis of the channel 570 and the surface of the foot. In this manner, an angled chisel with the known angle can be used to harvest the graft such that the graft forms a surface that is flush with the tibial plateau. A range of angled chisels can be made which covers a range, for example, from 15° to 45° in increments of 5°. When the surgeon places the foot flush against the tibial plateau, he notes the angle and selects an angled chisel with a similar angle to harvest the graft for that site. The tibial guide 520 also should be configured such that the second arm 545 is curved, or the combination of the second arm 545 and the extension 540 have a curved profile such that they will fit into the knee joint.

Figure 47:
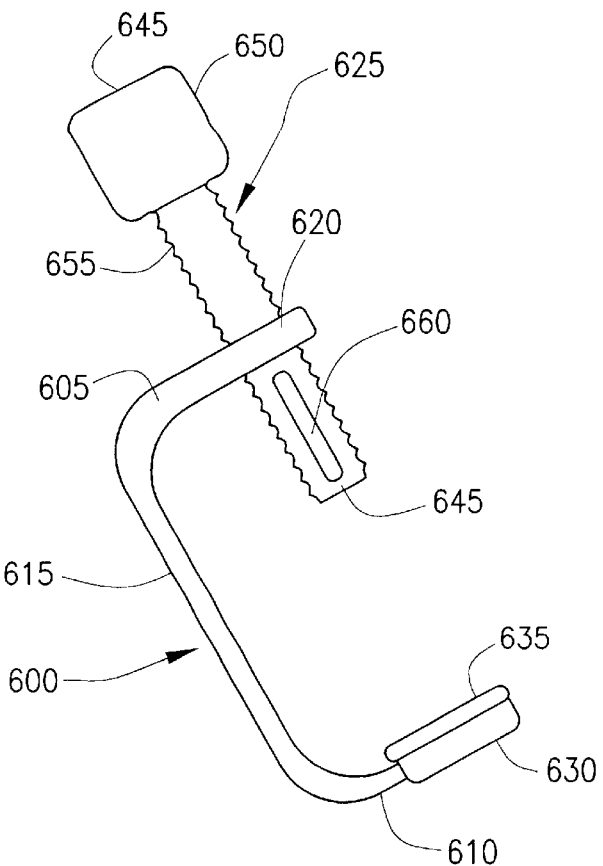
FIGS. 47–50 are views of a clamp body and a guide tube used in the repair of a patellar cartilage defect.
Figure 48:
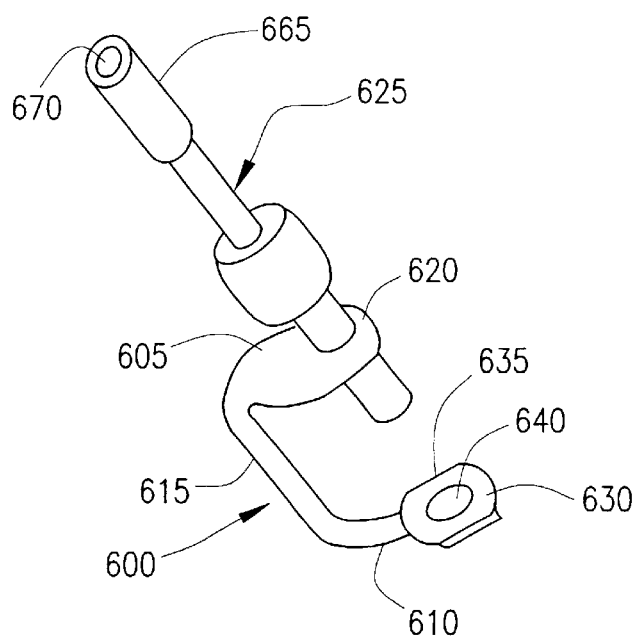

A number of embodiments of the invention have been described. Nevertheless, it will be understood that various modifications may be made without departing from the spirit and scope of the invention. For example, a guide and a handle can be configured to form a specific angle between a foot of the guide and a guide wire passed through the handle. Thus, referring to FIGS. 47–50, a guide may be configured as a clamp body 600 that includes an upper arm 605 and a lower arm 610 that are in a parallel orientation. The arms 605 and 610 each are joined at right angles by an extension 615. The upper arm 605 is wide and includes a threaded channel 620 through which a threaded, calibrated guide tube 625 is threadably inserted. The lower arm 610 includes a shoe 630 that has an upper surface 635. The shoe 630 may be fixed relative to the clamp body 600 or may include a pin through the lower arm 610 so that the shoe can pivot relative to the lower arm. If the shoe 630 is fixed, the upper surface 635 may be fixed at an angle relative to a longitudinal axis of the guide tube 625. As illustrated in FIG. 47, the upper surface 635 is at a perpendicular angle to the longitudinal axis of the guide tube 625. The shoe 630 also can be fixed at other angles. The shoe also includes a channel 640 passing through it.

Figure 49:
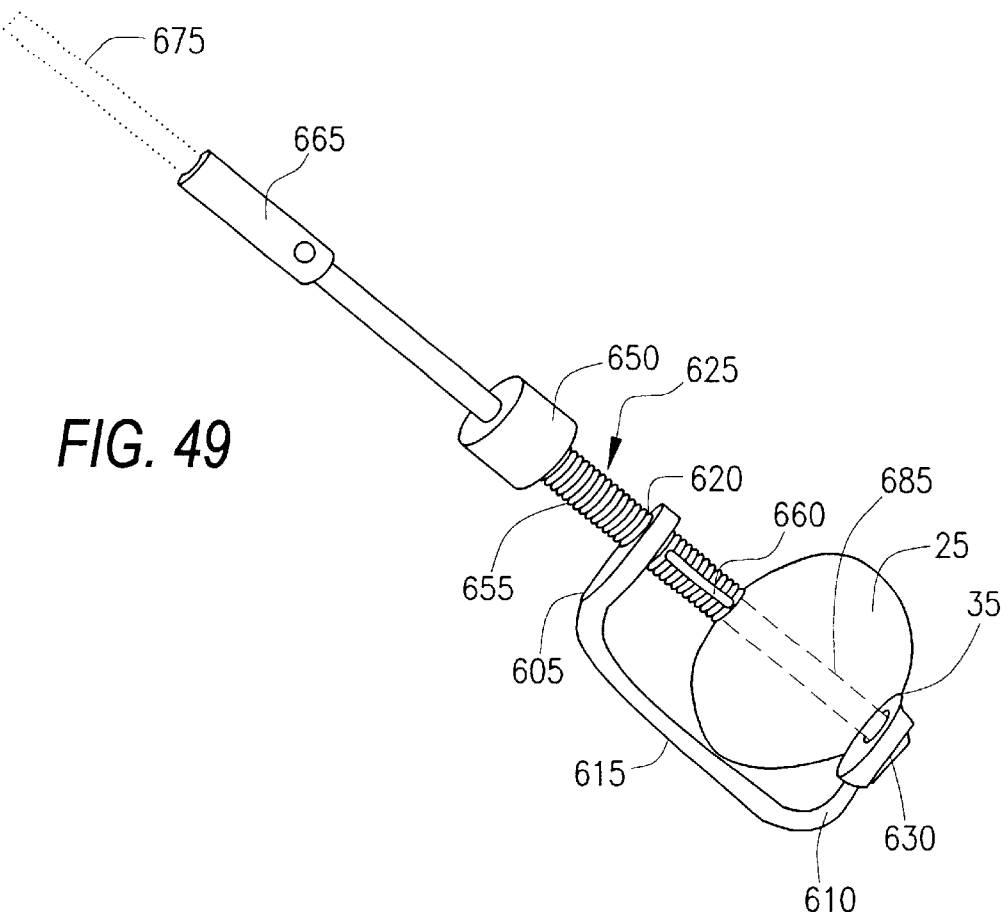
Figure 50:
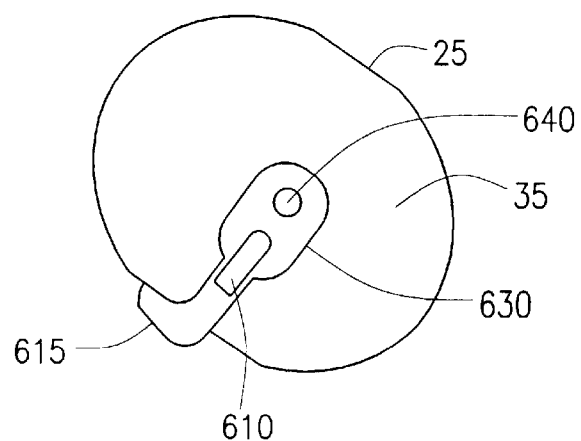

The guide tube 625 includes a channel 645 that passes along its longitudinal axis from a handle 650 and through a threaded tube 655. The threaded tube 655 includes a window 660 through which a guide wire or graft that is inserted through the channel 645 can be viewed. The channel 645 is configured to have a diameter that accepts a drill guide 665 (FIG. 48 and FIG. 49) having a channel 670 through which a guide wire 675 can be inserted (FIG. 49).

To use the instruments of FIGS. 47–50, the foot 630 is inserted through an incision and placed against the posterior surface 35 of the patella 25. When the upper surface 635 of the foot 630 is placed flush with the posterior surface 35 of the patella, the longitudinal axis of the guide tube will be perpendicular to the upper surface of the foot. The guide wire 675 then is inserted into the channel 670 through the drill guide 655, into an anterior incision, and used to drill a channel 685 through the patella 25.

The channel 685 is enlarged and a bone graft inserted according to the methods described above. If the delivery instruments are passed through the channel 645, the extent to which the graft is inserted can be viewed through the window 660. Because of the perpendicular relationship between the foot 630 and the longitudinal axis of the guide tube, the channel 685 is perpendicular to the posterior surface 35 of the patella surrounding the opening of the channel 685. If the foot 630 is set at a known angle to the longitudinal axis of the guide tube, the channel drilled will be at that angle to the posterior surface 35 of the patella. In that situation, the cartilage graft should be harvested such that its length forms a similar angle with its cartilage surface. With such a technique, the cartilage graft will be flush with the posterior surface 35 in which it is implanted.

Other embodiments are within the scope of the following claims.

What is claimed is:

1. A surgical method of repairing an articular cartilage surface on a posterior surface of the patella, comprising:
    placing a first instrument through a first incision so that the first instrument is adjacent to an anterior surface of the patella;
    placing a second instrument through a second incision so that the second instrument is located between the posterior surface of the patella and the femoral head;
    drilling a passage from the anterior surface of the patella to the posterior surface of the patella, wherein the passage passes between an anterior surface opening and a posterior surface opening;
    inserting a graft into the anterior surface opening of the passage; and
    inserting the graft further into the passage.

2. The surgical method of claim 1, wherein the first instrument includes a channel having a longitudinal axis that extends from the channel to the anterior surface opening of the patella, and through which a guide wire is inserted to drill the passage through the patella.

3. The surgical method of claim 2, wherein the second instrument is mountable to the first instrument and includes a surface that is configured to be placed against a posterior surface of the patella, wherein the longitudinal axis of the channel of the first instrument is approximately perpendicular to the surface of the second instrument when the second instrument is mounted in the first instrument.

4. The surgical method of claim 2, further comprising enlarging the drilled passage through the patella, wherein enlarging the passage comprises passing a drill over the guide wire, inserting the drill into the anterior surface opening, and enlarging the passage between the anterior surface opening and the posterior surface opening.

5. The surgical method of claim 1, wherein the passage through the patella is approximately perpendicular to the posterior surface of the patella adjacent to the posterior surface opening.

6. The surgical method of claim 1, wherein inserting the graft into the anterior surface opening of the passage further comprises placing a delivery instrument against the anterior surface opening, wherein the delivery instrument includes an interior channel that extends between an open distal end and an open proximal end, and a flange at the distal end, with the flange configured to be inserted into the anterior surface opening to deliver a cartilage graft through the interior channel into the passage in the patella.

7. The surgical method of claim 6, wherein the delivery instrument includes a window formed in a wall and open to the interior channel, whereby the cartilage graft can be visually inspected during delivery through the interior channel.

8. The surgical method of claim 6, wherein inserting the graft further into the passage comprises inserting an insertion instrument into the interior channel of the delivery instrument and advancing the cartilage graft from the delivery instrument into the passage in the patella through the anterior opening in the patella.

9. The surgical method of claim 1, wherein the first instrument comprises a director handle and a tube, the second instrument comprises a patellar guide including a foot having a generally flat surface, and the first and second instruments are assembled by installing the patellar guide in a slot of the director handle and inserting the tube in a channel of the director handle, wherein
    placing the first instrument adjacent to the anterior surface of the patella comprises placing a distal end of the tube against the anterior surface of the patella through a first incision; and
    placing the second instrument adjacent to the posterior surface of the patella comprises inserting the second instrument in a second incision and placing the generally flat surface of the foot against the posterior surface of the patella.

10. The surgical method of claim 9, further comprising inserting a guide wire through a longitudinal channel of the tube, inserting the guide wire into the first incision, and drilling a passage with the guide wire through the patella, wherein the passage passes between the anterior surface and the posterior surface of the patella.

11. The surgical method of claim 10, wherein the passage through the patella is perpendicular to the posterior surface of the patella.

12. The surgical method of claim 9, wherein the guide wire enters a channel in the foot when the guide wire passes through the posterior surface of the patella.

13. The surgical method of claim 9, further comprising removing the director handle and the patellar guide and inserting a drill over the guide wire to enlarge the passage through the patella.

14. The surgical method of claim 9, further comprising drilling at least one additional passage through the patella, wherein the additional passage is offset from the first passage.

15. The surgical method of claim 14, wherein drilling the additional passage comprises:

provided an offset tool comprising a handle having a distal end, a probe attached to the distal end and extending perpendicularly from a face of the handle, and a guide attached to the distal end, offset from the probe, and having an inner shaft with a longitudinal axis that is substantially parallel to the probe;

placing the probe in the first passage;

placing the guide wire through the bullet and through the inner shaft of the guide; and drilling the additional passage such that it is offset from the first passage by an offset distance from the probe and the longitudinal axis of the inner shaft.

16. The surgical method of claim 9, further comprising harvesting a cartilage replacement graft, wherein harvesting a cartilage graft comprises:

providing a chisel having a tip and a hollow longitudinal shaft passing through the chisel;

providing a chisel guard having a hollow shaft and a flanged end, wherein the shaft is configured to surround the chisel;

providing a tamp configured to be inserted into the longitudinal shaft of the chisel; and using the chisel to remove a cartilage graft from a surface of a bone, wherein the cartilage graft includes a cartilage surface and a bony shaft.

17. The surgical method of claim 16, further comprising transplanting the cartilage graft into the passage in the patella from the anterior surface of the patella to the posterior surface of the patella.

* * * * *